United States Patent [19]
Khanna et al.

[11] Patent Number: 5,935,990
[45] Date of Patent: Aug. 10, 1999

[54] SUBSTITUTED PYRROLYL COMPOUNDS FOR THE TREATMENT OF INFLAMMATION

[75] Inventors: Ish K. Khanna, Vernon Hills; Richard M. Weier, Lake Bluff; Yi Yu, Skokie, all of Ill.

[73] Assignee: G.D. Searle & Co., Chicago, Ill.

[21] Appl. No.: 08/987,356

[22] Filed: Dec. 9, 1997

Related U.S. Application Data

[60] Provisional application No. 60/032,688, Dec. 10, 1996.

[51] Int. Cl.$^6$ .......................... A61K 31/40; C07D 207/33
[52] U.S. Cl. .......................... 514/423; 514/424; 514/427; 548/560; 548/563; 548/561; 548/562
[58] Field of Search .................... 514/427, 423, 514/424; 548/560, 563

[56] References Cited

U.S. PATENT DOCUMENTS

| | | | |
|---|---|---|---|
| 3,168,531 | 2/1965 | Short | 260/326.3 |
| 3,427,305 | 2/1969 | Chinn | 260/239.6 |
| 3,531,497 | 9/1970 | Youngdale | 260/326.5 |
| 4,267,184 | 5/1981 | Cherkofsky | 424/263 |
| 4,267,190 | 5/1981 | Cherkofsky | 424/274 |
| 4,335,136 | 6/1982 | Cherkofsky | 424/274 |
| 4,652,582 | 3/1987 | Wilkerson | 514/427 |
| 4,694,018 | 9/1987 | Chinn | 514/427 |
| 5,032,590 | 7/1991 | Hubsch et al. | 514/248 |
| 5,096,919 | 3/1992 | Wasley et al. | 514/427 |
| 5,128,485 | 7/1992 | Kameswaran | 548/561 |
| 5,144,041 | 9/1992 | Doehner, Jr. | 548/531 |
| 5,187,185 | 2/1993 | Outcalt et al. | 514/408 |
| 5,219,856 | 6/1993 | Olson | 514/252 |
| 5,236,943 | 8/1993 | Heitsch et al. | 514/397 |
| 5,474,995 | 12/1995 | Ducharme et al. | 514/241 |
| 5,536,752 | 7/1996 | Ducharme et al. | 514/602 |
| 5,710,140 | 1/1998 | Ducharme et al. | 514/91 |

FOREIGN PATENT DOCUMENTS

| | | |
|---|---|---|
| 633582 | 4/1963 | Belgium . |
| 372982 | 6/1990 | European Pat. Off. . |
| 492093 | 10/1992 | European Pat. Off. . |
| 799823 | 10/1997 | European Pat. Off. . |
| 1938904 | 2/1970 | Germany . |
| 2261965 | 6/1973 | Germany . |
| 1263940 | 2/1972 | United Kingdom . |
| 94/15932 | 7/1994 | WIPO . |

OTHER PUBLICATIONS

H. Stetter and M. Schreckenberg, *Chem. Ber.*,. vol. 107, p. 2453, 1974.
F. Cerreto, et al., *Eur. J. Med. Chem.*, vol. 271, p. 7011, 1992.
M. Scalzo et al., *Il Farmaco Ed. Sc.*, vol. 43, p. 665, 1988.
M. Scalzo et al., *Il Farmaco Ed. Sc.*, vol. 43, p. 677, 1988.
M. Scalzo et al., *Eur. J. Med. Chem*, vol. 23, p. 587, 1988.
C. Gillet, et al., *Eur. J. Med. Chem*, vol. 11, p. 173, 1976.
G. Thiault et al., *Il Farmaco Ed. Sc.*, vol. 39, p. 524, 1984.
G. Thiault et al., *Il Farmaco Ed. Sc.*, vol. 39, p. 765, 1984.
W. Wilkerson et al., *Med. Chem. Res*, vol. 5, p. 399, 1995.
W. Wilkerson et al., *J. Med. Chem.*, vol. 38, p. 3895, 1995.
I. Khanna et al.., *J. Med Chem.*, vol. 40, p. 1619, 1997.
Buu–Hoi et al, *J. Med. Pharm. Chem.*, vol. 5, p. 1357, 1962.

*Primary Examiner*—Joseph K. McKane
*Attorney, Agent, or Firm*—Joseph W. Bulock

[57] ABSTRACT

A class of pyrrolyl derivatives is described for use in treating inflammation and inflammation-related disorders. Compounds of particular interest are defined by Formula I

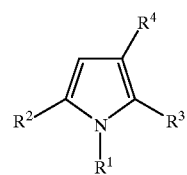

I wherein $R^1$, $R^2$, $R^3$ and $R^4$ are as described in the specification.

31 Claims, No Drawings

SUBSTITUTED PYRROLYL COMPOUNDS FOR THE TREATMENT OF INFLAMMATION

This application is based on provisional application Ser. No. 60/032,688 filed Dec. 10, 1996.

FIELD OF THE INVENTION

This invention is in the field of antiinflammatory pharmaceutical agents and specifically relates to compounds, compositions and methods for treating cyclooxygenase-2 mediated disorders, such as inflammation and arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

The references below that disclose antiinflammatory activity, show continuing efforts to find a safe and effective antiinflammatory agent. The novel pyrroles disclosed herein are such safe and also effective antiinflammatory agents furthering such efforts. The substituted pyrrolyl compounds disclosed herein preferably selectively inhibit cyclooxygenase-2 over cyclooxygenase-1.

Pyrroles have been described for various uses, including the treatment of inflammation.

U.S. Pat. No. 5,219,856, to R. Olson, generically describes pyrrole-containing angiotensin-II inhibitors. U.S. Pat. No. 5,236,943, to Heitsch et al., generically describes pyrrole containing angiotensin-II inhibitors.

U.S. Pat. No. 5,128,485, to V. Kameswaran, describes a process for preparing 2-phenyl-5-trifluoromethylpyrroles. EP 492093, published Jul. 1, 1992, describes a similar process.

U.S. Pat. No. 5,032,590, to Hubsch et al., describes 1,2-diphenyl-3-(4-fluorophenyl)-5-isopropylpyrrole as an intermediate in the preparation of a hydroxylamine substituted pyrrole.

H. Stetter and M. Schreckenberg (*Chem. Ber.*, 107, 2453 (1974)] describe the synthetic preparation of 1,2-diaryl pyrroles, and specifically, 2-(4-chlorophenyl)-5-methyl-1-phenylpyrrole. F. Cerreto, et al. [*Eur. J. Med. Chem*, 27, 701 (1992)] describe the 1,5-diaryl-2-methylpyrroles as having anti-Candida activity. M. Scalzo et al. [*Il Farmaco Ed. Sc.,* 43, 665 (1988)] describe 1,5-substituted pyrroles as having antibacterial activity. M. Scalzo et al. [*Il Farrmaco Ed. Sc.,* 43, 677 (1988)] describe other 1,5-substituted pyrroles as having antibacterial activity. M. Scalzo et al. [*Eur. J. Med. Chem*, 23, 587 (1988)] describe 2-methyl-5-(4-nitrophenyl)-1-phenylpyrroles as having antibacterial activity.

C. Gillet, et al [*Eur. J. Med. Chem*, 11, 173 (1976)] describe the 1,5-diaryl-3-pyrrole acetic acids as having antiinflammatory activity. German Patent DE 2,261,965 describes 2-methyl-1-phenylpyrroles as having antiinflammatory activity. Belgian Patent 633,582 describes 1-aryl-5-(4-alkoxyphenyl)-2-pyrrole propanoic acids as anticholesterolaemic agents. G. Thiault et al. [*Il Farmaco Ed. Sc.,* 39, 524 (1984)] describe 1,5-substituted pyrroles as having analgesic and antiinflammatory activity. G. Thiault et al. [*Il Farmaco Ed. Sc.,* 39, 765 (1984)] describe other 1,5-substituted pyrroles as having analgesic and antiinflammatory activity. U.S. Pat. No. 4,694,018, issued to L. Chin, describes 1-(halophenyl)-5-phenyl-2-pyrrole propanoic acid derivatives as 5-lipoxygenase inhibitors. U.S. Pat. No. 5,096,919, issued to Wasley et al., describes 1-pyrrole phenyl hydroxamic acid derivatives as 5-lipoxygenase inhibitors.

U.S. Pat. No. 4,267,184, issued to S. Cherkofsky, describes 4,5-aryl-2-thiopyrroles as antiinflammatory agents. U.S. Pat. No. 4,267,190, issued to S. Cherkofsky, describes 4,5-aryl-2-methanethiolpyrroles as antiinflammatory agents. U.S. Pat. No. 4,335,136, issued to S. Cherkofsky, describes 4,5-aryl-2-methanaminepyrroles as antiinflammatory agents. U.S. Pat. No. 4,267,184, issued to S. Cherkofsky, describes 4,5-aryl-2-halopyrroles as antiinflammatory agents. U.S. Pat. No. 3,531,497, issued to G. Youngdale, describes 2,4,5-triphenylpyrroles as antiinflammatory agents. U.S. Pat. No. 4,267,184, issued to S. Cherkofsky, describes 4,5-phenylpyrroles as antiinflammatory agents. U.S. Pat. No. 5,474,995, issued to Ducharme et al., describes 4,5-phenylpyrroles as cyclooxygenase-2 inhibitors. W. Wilkerson et al. *Med. Chem. Res,.* 5, 399 (1995)] describe 4,5-diarylpyrroles as COX-2 inhibitors. W. Wilkerson et al. *J. Med. Chem.,* 38, 3895 (1995)] describe 4,5-diarylpyrroles as COX-2 inhibitors. PCT patent document WO94/15932, published Jul. 21, 1994, describes 3,4-diphenylpyrroles as inhibiting cyclooxygenase-2.

U.S. Pat. No. 5,187,185, to outcalt, et al., describes substituted 1-arylpyrroles as pesticides. European patent document EP 372,982, published Jun. 13, 1990, describes similar compounds.

U.S. Pat. No. 3,427,305, to L. Chinn, describes 1-[4-(aminosulfonyl)phenyl]pyrrole propanoic acids as being antiinflammatory. Specifically, 1-(4-(aminosulfonyl)phenyl]-5-(4-fluorophenyl)-2-pyrrole propanoic acid is described.

British patent GB 1,263,940 describes 1-phenylpyrroles as having antiinflammatory activity. Specifically, 4-[2-methyl-5-phenylpyrrol-1-yl]benzenesulfonamide is described.

The invention's pyrrolyl compounds are found to show usefulness as antiinflammatory agents with minimal side effects.

DESCRIPTION OF THE INVENTION

A class of substituted pyrrolyl compounds useful in treating inflammation-related disorders is defined by Formula I:

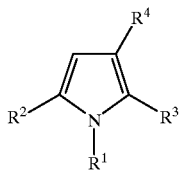

wherein $R^1$ and $R^2$ are independently selected from aryl, cycloalkyl, cycloalkenyl and heterocyclyl, wherein $R^1$ and $R^2$ are optionally substituted at a substitutable position with one or more radicals independently selected from alkylsulfonyl, aminosulfonyl, haloalkylsulfonyl, halo, alkylthio, alkylsulfinyl, alkyl, cyano, carboxyl, alkoxycarbonyl, haloalkyl, hydroxyl, alkoxy, hydroxyalkyl, alkoxyalkyl, alkylcarbonyl, haloalkoxy, amino, alkylamino, arylamino and nitro;

wherein $R^3$ is a radical selected from hydrido, halo, methyl and alkoxycarbonylalkyl; and wherein $R^4$ is a radical selected from hydrido, halo, alkyl, haloalkyl, cyano, alkoxycarbonyl, carboxyl, formyl, aryl, heteroaryl, aralkyl, heteroarylalkyl, alkylsulfonyl, haloalkylsulfonyl, arylsulfonyl, heteroarylsulfonyl, hydroxyalkyl, mercaptoalkyl, alkoxyalkyl, aryloxyalkyl, heteroaryloxyalkyl, aralkyloxyalkyl, heteroarylalkyloxyalkyl, alkylthioalkyl, arylthioalkyl, heteroarylthioalkyl, aralkylthioalkyl, heteroarylalkylthioalkyl, haloalkylcarbonyl, haloalkyl(hydroxy)alkyl, alkylcarbonyl, arylcarbonyl, aralkylcarbonyl, heteroarylcarbonyl, heteroarylalkylcarbonyl, carboxyalkyl, alkoxycarbonylalkyl, alkylcarbonyloxyalkyl, aminoalkyl, alkylaminoalkyl, arylaminoalkyl, aralkylaminoalkyl, heteroarylaminoalkyl, heteroarylalkylaminoalkyl, alkoxy, and aryloxy;

provided at least one of $R^1$ and $R^2$ is phenyl substituted with methylsulfonyl or aminosulfonyl; and further provided $R^3$ is hydrido when $R^1$ is phenyl substituted with aminosulfonyl or methylsulfonyl;

or a pharmaceutically-acceptable salt thereof.

Compounds of Formula I would be useful for, but not limited to, the treatment of inflammation in a subject, and for treatment of other cyclooxygenase-2 mediated disorders, such as, as an analgesic in the treatment of pain and headaches, or as an antipyretic for the treatment of fever. For example, compounds of the invention would be useful to treat arthritis, including but not limited to rheumatoid arthritis, spondyloarthropathies, gouty arthritis, osteoarthritis, systemic lupus erythematosus and juvenile arthritis. Such compounds of the invention would be useful in the treatment of asthma, bronchitis, menstrual cramps, premature labor, tendinitis, bursitis, skin-related conditions such as psoriasis, eczema, burns and dermatitis, and from post-operative inflammation including from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis. Compounds of the invention would be useful for the prevention or treatment of cancer, such as colorectal cancer, and cancer of the breast, lung, prostate, bladder, cervix and skin. Compounds of the invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as retinitis, retinopathies, uveitis, ocular photophobia, and of acute injury to the eye tissue. The compounds would also be useful in the treatment of pulmonary inflammation, such as that associated with viral infections and cystic fibrosis. The compounds would also be useful for the treatment of certain central nervous system disorders, such as cortical dementias including Alzheimer's disease, and central nervous system damage resulting from stroke, ischemia and trauma. The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, and atherosclerosis. The compounds would also be useful in the treatment of pain, but not limited to postoperative pain, dental pain, muscular pain, and pain resulting from cancer.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in place of other conventional antiinflammatories, such as together with steroids, NSAIDs, 5-lipoxygenase inhibitors, $LTB_4$ receptor antagonists and $LTA_4$ hydrolase inhibitors.

Suitable $LTA_4$ hydrolase inhibitors include RP-64966, (S,S)-3-amino-4-(4-benzyloxyphenyl)-2-hydroxybutyric acid benzyl ester (Scripps Res. Inst.), N-(2(R)-(cyclohexylmethyl)-3-(hydroxycarbamoyl)propionyl)-L-alanine (Searle), 7-(4-(4-ureidobenzyl)phenyl)heptanoic acid (Rhone-Poulenc Rorer), and 3-(3-(1E,3E-tetradecadienyl)-2-oxiranyl)benzoic acid lithium salt (Searle).

Suitable $LTB_4$ receptor antagonists include, among others, ebselen, linazolast, ontazolast, Bayer Bay-x-1005, Ciba Geigy compound CGS-25019C, Leo Denmark compound ETH-615, Merck compound MAFP, Terumo compound TMK-688, Tanabe compound T-0757, Lilly compounds LY-213024, LY-210073, LY223982, LY233469, and LY255283, LY-293111, 264086 and 292728, ONO compounds ONO-LB457, ONO-4057, and ONO-LB-448, Shionogi compound S-2474, calcitrol, Lilly compounds Searle compounds SC-53228, SC-41930, SC-50605 and SC-51146, Warner Lambert compound BPC 15, SmithKline Beecham compound SB-209247 and SK&F compound SKF-104493. Preferably, the $LTB_4$ receptor antagonists are selected from calcitrol, ebselen, Bayer Bay-x-1005, Ciba Geigy compound CGS-25019C, Leo Denmark compound ETH-615, Lilly compound LY-293111, Ono compound ONO-4057, and Terumo compound TMK-688.

Suitable 5-LO inhibitors include, among others, Abbott compounds A-76745, 78773 and ABT761, Bayer Bay-x-1005, Cytomed CMI-392, Eisai E-3040, Scotia Pharmaceutica EF-40, Fujirebio F-1322, Merckle ML-3000, Purdue Frederick PF-5901, 3M Pharmaceuticals R-840, rilopirox, flobufen, linasolast, lonapolene, masoprocol, ontasolast, tenidap, zileuton, pranlukast, tepoxalin, rilopirox, flezelastine hydrochloride, enazadrem phosphate, and bunaprolast.

The present compounds may also be used in combination therapies with opioids and other analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists and sodium channel blockers, among others. More preferred would be combinations with compounds selected from morphine, meperidine, codeine, pentazocine, buprenorphine, butorphanol, dezocine, meptazinol, hydrocodone, oxycodone, methadone, Tramadol [(+) enantiomer], DuP 747, Dynorphine A, Enadoline, RP-60180, HN-11608, E-2078, ICI-204448, acetominophen (paracetamol), propoxyphene, nalbuphine, E-4018, filenadol, mirfentanil, amitriptyline, DuP631, Tramadol [(−) enantiomer], GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, and CP-99,994.

The present invention preferably includes compounds which selectively inhibit cyclooxygenase-2 over cyclooxygenase-1. Preferably, the compounds have a cyclooxygenase-2 $IC_{50}$ equal to or less than about 0.2 $\mu$M, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 1.0 $\mu$M, and more preferably of greater than 10 $\mu$M. Such preferred selectivity may indicate an ability to reduce the incidence of common NSAID-induced side effects.

A preferred class of compounds consists of those compounds of Formula I wherein $R^1$ and $R^2$ are independently selected from phenyl, lower cycloalkyl, lower cycloalkenyl and 5- or 6-membered heteroaryl, wherein $R^1$ and $R^2$ are optionally substituted at a substitutable position with one or more radicals independently selected from lower alkylsulfonyl, aminosulfonyl, lower haloalkylsulfonyl, halo, lower alkylthio, lower alkyl, cyano, carboxyl, lower alkoxycarbonyl, lower alkylcarbonyl, lower haloalkyl, hydroxyl, lower alkoxy, lower hydroxyalkyl, lower alkoxyalkyl, lower haloalkoxy, amino, lower alkylamino, arylamino and nitro; wherein $R^3$ is a radical selected from hydrido, halo, methyl and lower alkoxycarbonylalkyl; and wherein $R^4$ is a radical selected from hydrido, halo, lower alkyl, lower haloalkyl, cyano, lower alkoxycarbonyl, carboxyl, formyl, phenyl, 5- or 6-membered heteroaryl, lower aralkyl, lower heteroarylalkyl, lower alkylsulfonyl, lower haloalkylsulfonyl, phenylsulfonyl, 5- or 6-membered heteroarylsulfonyl, lower hydroxyalkyl, lower mercaptoalkyl, lower alkoxyalkyl, lower phenyloxyalkyl, lower heteroaryloxyalkyl, lower aralkyloxyalkyl, lower heteroarylalkyloxyalkyl, lower alkylthioalkyl, lower phenylthioalkyl, lower heteroarylthioalkyl, lower aralkylthioalkyl, lower heteroarylalkylthioalkyl, lower haloalkylcarbonyl, lower haloalkyl(hydroxy)alkyl, lower alkylcarbonyl, phenylcarbonyl, lower aralkylcarbonyl, 5- or 6-membered heteroarylcarbonyl, 5- or 6-membered heteroarylalkylcarbonyl, lower carboxyalkyl, lower alkoxycarbonylalkyl, lower alkylcarbonyloxyalkyl, lower aminoalkyl, lower alkylaminoalkyl, lower phenylaminoalkyl, lower aralkylaminoalkyl, lower heteroarylaminoalkyl, lower heteroarylalkylaminoalkyl, lower alkoxy, and phenyloxy; or a pharmaceutically-acceptable salt thereof.

A class of compounds of particular interest consists of those compounds of Formula I wherein $R^1$ and $R^2$ are independently selected from phenyl, cyclohexyl, cyclohexenyl, benzofuryl, benzodioxolyl, furyl, imidazolyl, thienyl, thiazolyl, pyrrolyl, oxazolyl, isoxazolyl, triazolyl, pyrimidinyl, isoquinolyl, quinolinyl, benzimidazolyl, indolyl, pyrazolyl and pyridyl, wherein $R^1$ and $R^2$ are optionally substituted at a substitutable position with one or more radicals independently selected from methylsulfonyl, aminosulfonyl, fluoromethylsulfonyl, difluoromethylsulfonyl, fluoro, chloro, bromo, methylthio, methyl, ethyl, isopropyl, tert-butyl, isobutyl, pentyl, hexyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, methylcarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl, hydroxyethyl, methoxymethyl, ethoxymethyl, trifluoromethoxy, amino, methylamino, N,N-dimethylamino, phenylamino and nitro; wherein $R^3$ is a radical selected from hydrido, fluoro, chloro, bromo, methyl, ethoxycarbonylethyl, and methoxycarbonylmethyl; and wherein $R^4$ is a radical selected from hydrido, fluoro, chloro, bromo, methyl, ethyl, fluoromethyl, difluoromethyl, trifluoromethyl, cyano, methoxycarbonyl, ethoxycarbonyl, tert-butoxycarbonyl, carboxyl, formyl, phenyl, benzyl, phenylethyl, phenylpropyl, methylsulfonyl, phenylsulfonyl, trifluoromethylsulfonyl, hydroxymethyl, hydroxyethyl, methoxymethyl, ethoxymethyl, methylcarbonyl, ethylcarbonyl, trifluoromethylcarbonyl, trifluoro(hydroxy) ethyl, phenylcarbonyl, benzylcarbonyl, methoxycarbonylmethyl, ethoxycarbonylethyl, carboxymethyl, carboxypropyl, methylcarbonyloxymethyl, phenyloxy, phenyloxymethyl, thienyl, furyl, and pyridyl, wherein the thienyl, furyl, pyridyl and phenyl radicals are optionally substituted at a substitutable position with one or more radicals selected from fluoro, chloro, bromo, methylthio, methylsulfinyl, methyl, ethyl, isopropyl, tert-butyl, isobutyl, pentyl, hexyl, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl, hydroxyethyl and trifluoromethoxy; or a pharmaceutically-acceptable salt thereof.

Within Formula I there is a subclass of compounds of high interest represented by Formula II:

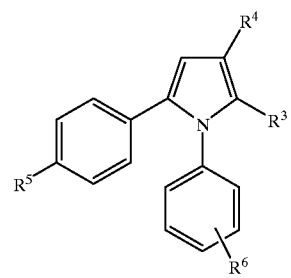

wherein $R^3$ is a radical selected from hydrido, methyl and lower alkoxycarbonylalkyl; wherein $R^4$ is a radical selected from hydrido, halo, cyano, formyl, lower haloalkylsulfonyl, lower haloalkyl, lower hydroxyalkyl, lower alkylcarbonyl, lower aryloxyalkyl, lower haloalkylcarbonyl, phenylcarbonyl, lower alkylcarbonyloxyalkyl and lower haloalkylhydroxyalkyl; wherein $R^5$ is methylsulfonyl or aminosulfonyl; and wherein $R^6$ is one or more radicals independently selected from hydrido, halo, lower alkyl, lower alkylcarbonyl, and lower haloalkyl; or a pharmaceutically-acceptable salt thereof.

A class of compounds of particular interest consists of those compounds of Formula II wherein $R^3$ is a radical selected from hydrido, methyl and ethoxycarbonylethyl; wherein $R^4$ is a radical selected from hydrido, trifluoroethyl, chloro, bromo, formyl, cyano, trifluoromethylsulfonyl, hydroxymethyl, methylcarbonyl, phenylcarbonyl, phenyloxymethyl, trifluoromethylcarbonyl, trifluoro (hydroxy)ethyl and methylcarbonyloxymethyl; wherein $R^5$ is methylsulfonyl or aminosulfonyl; and wherein $R^6$ is one or more radicals independently selected from hydrido, fluoro, chloro, methyl, ethyl, trifluoromethyl and methylcarbonyl; or a pharmaceutically-acceptable salt thereof.

Within Formula I there is a second subclass of compounds of high interest represented by Formula III:

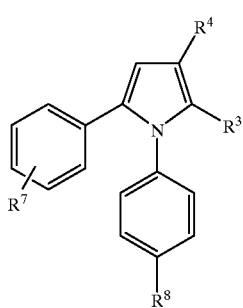

III wherein $R^3$ is hydrido; wherein $R^4$ is a radical selected from hydrido, halo, cyano, formyl, lower haloalkylsulfonyl, lower haloalkyl, lower hydroxyalkyl, lower alkylcarbonyl, lower haloalkylcarbonyl, phenylcarbonyl, lower aryloxyalkyl, lower alkylcarbonyloxyalkyl and lower haloalkylhydroxyalkyl; wherein $R^7$ is one or more radicals independently selected from hydrido, halo, lower alkyl, lower alkylcarbonyl, and lower haloalkyl; and wherein $R^8$ is methylsulfonyl or aminosulfonyl; or a pharmaceutically-acceptable salt thereof.

A class of compounds of particular interest consists of those compounds of Formula III wherein $R^3$ is hydrido; wherein $R^4$ is a radical selected from hydrido, trifluoroethyl, chloro, bromo, formyl, cyano, trifluoromethylsulfonyl, hydroxymethyl, methylcarbonyl, phenylcarbonyl, phenyloxymethyl, trifluoromethylcarbonyl, trifluoro (hydroxy)ethyl and methylcarbonyloxymethyl; wherein $R^7$ is one or more radicals independently selected from hydrido, fluoro, chloro, methyl, ethyl, trifluoromethyl and methylcarbonyl; and wherein $R^8$ is methylsulfonyl or aminosulfonyl; or a pharmaceutically-acceptable salt thereof.

A family of specific compounds of particular interest within Formula I consists of compounds and pharmaceutically-acceptable salts thereof as follows:
1-(4-fluorophenyl)-2-methyl-5-[4-(methylsulfonyl)phenyl]-1H-pyrrole;
2-methyl-5-[4-(methylsulfonyl)phenyl]-1-phenyl-1H-pyrrole;
1-(3,4-difluorophenyl)-2-methyl-5-[4-(methylsulfonyl)phenyl]-1H-pyrrole;
2-methyl-5-[4-(methylsulfonyl)phenyl]-1-[4-(trifluoromethyl)phenyl]-1H-pyrrole;
2-methyl-1-(4-methylphenyl)-5-[4-(methylsulfonyl)phenyl]-1H-pyrrole;
1-[4-[2-methyl-5-[4-(methylsulfonyl)phenyl]-1H-pyrrol-1-yl]phenyl]ethanone;
1-cyclohexyl-2-methyl-5-[4-(methylsulfonyl)phenyl]-1H-pyrrole;
2-(4-fluorophenyl)-1-[4-(methylsulfonyl)phenyl]-1H-pyrrole;
4-[2-(4-fluorophenyl)-1H-pyrrol-1-yl]benzenesulfonamide;
1-(4-fluorophenyl)-2-[4-(methylsulfonyl)phenyl]-1H-pyrrole;
4-[1-(4-fluorophenyl)-5-methyl-1H-pyrrol-2-yl]benzenesulfonamide;
ethyl 1-(4-fluorophenyl)-5-[4-(methylsulfonyl)phenyl]-1H-pyrrole-2-propanoate;
2,2,2-trifluoro-1-[1-(4-fluorophenyl)-2-methyl-5-[4-(methylsulfonyl)phenyl]-1H-pyrrol-3-yl]ethanone;
1-[1-(4-fluorophenyl)-2-methyl-5-[4-(methylsulfonyl)phenyl]-1H-pyrrol-3-yl]ethanone;
1-(4-fluorophenyl)-2-methyl-5-[4-(methylsulfonyl)phenyl]-1H-pyrrol-3-yl]-phenylmethanone;
1-(4-fluorophenyl)-2-methyl-5-[4-5 (methylsulfonyl)phenyl]-3-[(trifluoromethyl)sulfonyl]-1H-pyrrole;
1-(4-fluorophenyl)-2-methyl-5-[4-(methylsulfonyl)phenyl]-1H-pyrrole-3-carbonitrile;
1-(4-fluorophenyl)-2-methyl-5-[4-10 (methylsulfonyl)phenyl]-1H-pyrrole-3-carboxaldehyde;
3-bromo-1-(4-fluorophenyl)-2-methyl-5-[4-(methylsulfonyl)phenyl]-1H-pyrrole;
3-chloro-1-(4-fluorophenyl)-2-methyl-5-[-4-(methylsulfonyl)phenyl]-1H-pyrrole;
1-(4-fluorophenyl)-2-methyl-5-[4-(methylsulfonyl)phenyl]-1H-pyrrole-3-methanol;
[1-(4-fluorophenyl)-2-methyl-5-[4-(methylsulfonyl)phenyl]-1H-pyrrol-3-yl]methyl acetate;
1-(4-fluorophenyl)-2-methyl-5-[4-20 (methylsulfonyl)phenyl] -α,α,α- (trifluoromethyl)-1H-pyrrole-3-methanol;
1-(4-fluorophenyl)-2-methyl-5-[4-(methylsulfonyl)phenyl]-3-(2,2,2-trifluoroethyl)-1H-pyrrole;
3-[(3-chlorophenoxy)methyl]-1-(4-fluorophenyl)-2-methyl-5-[4-methylsulfonyl)phenyl]-1H-pyrrole;
3-[(4-chlorophenoxy)methyl]-1-(4-fluorophenyl)-2-methyl-5-[4-(methylsulfonyl)phenyl]-1H-pyrrole;
3-fluoro-1-(4-fluorophenyl)-2-methyl-5-[-4-(methylsulfonyl)phenyl]-1H-pyrrole;
2-methyl-5-[4-(methylsulfonyl)phenyl]-1-(4-pyridyl)-1H-pyrrole;
2-methyl-5-[4-(methylsulfonyl)phenyl]-1-(3-pyridyl)-1H-pyrrole;
2-methyl-5-[4-(methylsulfonyl)phenyl]-1-(2-pyridyl)-1H-pyrrole;
2-methyl-5- [4- (methylsulfonyl)phenyl] -1- (4-methyl-2-pyridyl)-1H-pyrrole;
2-methyl-5-[4-(methylsulfonyl)phenyl]-1-(4-methyl-3-pyridyl)-1H-pyrrole;
2-methyl-5-[4-(methylsulfonyl)phenyl]-1-(5-methyl-2-pyridyl)-1H-pyrrole;
2-methyl-5-[4-(methylsulfonyl)phenyl]-1-(5-methyl-3-pyridyl)-1H-pyrrole;
2-methyl-5-[4-(methylsulfonyl)phenyl]-1-(3-methyl-2-pyridyl)-1H-pyrrole;
2-methyl-5-[4-(methylsulfonyl)phenyl]-1-(2-methyl-3-pyridyl)-1H-pyrrole;
1-(4-chlorophenyl)-2-methyl-5-[4-(methylsulfonyl)phenyl]-1H-pyrrole;

2-methyl-1-(4-methylthiophenyl)-5-[4-(methylsulfonyl)phenyl]-1H-pyrrole;
2-methyl-1-(4-methylsulfinylphenyl)-5-[4-(methylsulfonyl)phenyl]-1H-pyrrole;
1-(4-methoxyphenyl)-2-methyl-5-[4-(methylsulfonyl)phenyl)-1H-pyrrole;
1-(3-fluoro-4-methoxyphenyl)-2-methyl-5-[4-(methylsulfonyl)phenyl]-1H-pyrrole;
1-(3-chloro-4-methoxyphenyl)-2-methyl-5-[4-(methylsulfonyl)phenyl]-1H-pyrrole;
1-(3,5-dichloro-4-methoxyphenyl)-2-methyl-5-[4-(methylsulfonyl)phenyl]-1H-pyrrole;
1-(3,5-difluoro-4-methoxyphenyl)-2-methyl-5-[4-(methylsulfonyl)phenyl]-1H-pyrrole;
1-(3-chloro-4-fluorophenyl)-2-methyl-5-[4-(methylsulfonyl)phenyl]-1H-pyrrole;
1-(4-hydroxyphenyl)-2-methyl-5-[4-(methylsulfonyl)phenyl]-1H-pyrrole;
1-(4-hydroxymethylphenyl)-2-methyl-5-[4-(methylsulfonyl)phenyl]-1H-pyrrole;
1-[4-[2-methyl-5-[4-(aminosulfonyl)phenyl]-1H-pyrrol-1-yl]phenyl]ethanone;
4-[1-(cyclohexyl)-2-methyl-1H-pyrrol-5-yl]benzenesulfonamide;
4-[1-phenyl-2-methyl-1H-pyrrol-5-yl]benzenesulfonamide;
4-[1-(3,4-difluorophenyl)-2-methyl-1H-pyrrol-5-yl]benzenesulfonamide;
4-[1-(4-trifluoromethylphenyl)-2-methyl-1H-pyrrol-5-yl]benzenesulfonamide;
4-[1-(4-methylphenyl)-2-methyl-1H-pyrrol-5-yl]benzenesulfonamide;
4-[2-methyl-1-(4-pyridyl)-1H-pyrrol-5-yl]benzenesulfonamide;
4-[1-(4-chlorophenyl)-2-methyl-1H-pyrrol-5-yl]benzenesulfonamide;
4-[2-methyl-1-(4-methylthiophenyl)-1H-pyrrol-5-yl]benzenesulfonamide;
4-[2-methyl-1-(4-methylsulfinylphenyl)-1H-pyrrol-5-yl]benzenesulfonamide;
4-[1-(4-methoxyphenyl)-2-methyl-1H-pyrrol-5-yl]benzenesulfonamide;
4-[1-(3-fluoro-4-methoxyphenyl)-2-methyl-1H-pyrrol-5-yl]benzenesulfonamide;
4-[1-(3-chloro-4-methoxyphenyl)-2-methyl-1H-pyrrol-5-yl]benzenesulfonamide;
4-[1-(3,5-dichloro-4-methoxyphenyl)-2-methyl-1H-pyrrol-5-yl]benzenesulfonamide;
4-[1-(3,5-difluoro-4-methoxyphenyl)-2-methyl-1H-pyrrol-5-yl]benzenesulfonamide;
4-[1-(3-chloro-4-fluorophenyl)-2-methyl-1H-pyrrol-5-yl]benzenesulfonamide;
4-[1-(4-hydroxyphenyl)-2-methyl-1H-pyrrol-5-yl]benzenesulfonamide;
4-[1-(4-hydroxymethylphenyl)-2-methyl-1H-pyrrol-5-yl]benzenesulfonamide;
5-[4-(methylsulfonyl)phenyl]-1-(4-pyridyl)-1H-pyrrole;
5-[4-(methylsulfonyl)phenyl]-1-(3-pyridyl)-1H-pyrrole;
5-[4-(methylsulfonyl)phenyl]-1-(2-pyridyl)-1H-pyrrole;
5-[4-(methylsulfonyl)phenyl]-1-(4-methyl-2-pyridyl)-1H-pyrrole;
5-[4-(methylsulfonyl)phenyl]-1-(4-methyl-3-pyridyl)-1H-pyrrole;
5-[4-(methylsulfonyl)phenyl]-1-(5-methyl-2-pyridyl)-1H-pyrrole;
5-[4-(methylsulfonyl)phenyl]-1-(5-methyl-3-pyridyl)-1H-pyrrole;
5-[4-(methylsulfonyl)phenyl]-1-(3-methyl-2-pyridyl)-1H-pyrrole;
5-[4-(methylsulfonyl)phenyl]-1-(2-methyl-3-pyridyl)-1H-pyrrole;
1-(4-chlorophenyl)-5-[4-(methylsulfonyl)phenyl]-1H-pyrrole;
1-(4-methylthiophenyl)-5-[4-(methylsulfonyl)phenyl]-1H-pyrrole;
1-(4-methylsulfinylphenyl)-5-[4-(methylsulfonyl)phenyl]-1H-pyrrole;
1-(4-methoxyphenyl)-5-[4-(methylsulfonyl)phenyl]-1H-pyrrole;
1-(3-fluoro-4-methoxyphenyl)-5-[4-(methylsulfonyl)phenyl]-1H-pyrrole;
1-(3-chloro-4-methoxyphenyl)-5-[4-(methylsulfonyl)phenyl]-1H-pyrrole;
1-(3,5-dichloro-4-methoxyphenyl)-5-[4-(methylsulfonyl)phenyl]-1H-pyrrole;
1-(3,5-difluoro-4-methoxyphenyl)-5-[4-(methylsulfonyl)phenyl]-1H-pyrrole;
1-(3-chloro-4-fluorophenyl)-5-[4-(methylsulfonyl)phenyl]-1H-pyrrole;
1-(4-hydroxyphenyl)-5-[4-(methylsulfonyl)phenyl]-1H-pyrrole;
1-(4-hydroxymethylphenyl)-5-[4-(methylsulfonyl)phenyl]-1H-pyrrole;
1-[4-[5-[4-(aminosulfonyl)phenyl]-1H-pyrrol-1-yl]phenyl]ethanone;
4-(1-(4-fluorophenyl)-2-methyl-3-[(trifluoromethyl)sulfonyl]-1H-pyrrol-5-yl]benzenesulfonamide;
4-[3-bromo-1-(4-fluorophenyl)-2-methyl-1H-pyrrol-5-yl]benzenesulfonamide;
4-[3-chloro-1-(4-fluorophenyl)-2-methyl-1H-pyrrol-5-yl]benzenesulfonamide;
4-[1-(4-fluorophenyl)-2-methyl-3-trifluoromethyl-1H-pyrrol-5-yl)benzenesulfonamide;
4-[1-(4-fluorophenyl)-2-methyl-3-difluoromethyl-1H-pyrrol-5-yl]benzenesulfonamide;
2-[2,2-trifluoro-1-[1-(4-fluorophenyl)-2-methyl-5-(4-(aminosulfonyl)phenyl]-1H-pyrrol-3-yl]ethanone;
4-[1-(cyclohexyl)-1H-pyrrol-5-yl]benzenesulfonamide;
4-[1-phenyl-1H-pyrrol-5-yl]benzenesulfonamide;
4-[1-(3,4-difluorophenyl)-1H-pyrrol-5-yl]benzenesulfonamide;
4-[1-(4-trifluoromethylphenyl)-1H-pyrrol-5-yl]benzenesulfonamide;
4-[1-(4-methylphenyl)-1H-pyrrol-5-yl]benzenesulfonamide;
4-[1-(4-pyridyl)-1H-pyrrol-5-yl]benzenesulfonamide;
4-[1-(4-chlorophenyl)-1H-pyrrol-5-yl]benzenesulfonamide;
4-[1-(4-methylthiophenyl)-1H-pyrrol-5-yl]benzenesulfonamide;
4-[1-(4-methylsulfinylphenyl)-1H-pyrrol-5-yl]benzenesulfonamide;
4-[1-(4-methoxyphenyl)-1H-pyrrol-5-yl]benzenesulfonamide;
4-[1-(3-fluoro-4-methoxyphenyl)-1H-pyrrol-5-yl]benzenesulfonamide;
4-[1-(3-chloro-4-methoxyphenyl)-1H-pyrrol-5-yl]benzenesulfonamide;
4-[1-(3,5-dichloro-4-methoxyphenyl)-1H-pyrrol-5-yl]benzenesulfonamide;
4-[1-(3,5-difluoro-4-methoxyphenyl)-1H-pyrrol-5-yl]benzenesulfonamide;
4-[1-(3-chloro-4-fluorophenyl)-1H-pyrrol-5-yl]benzenesulfonamide;
4-[1-(4-hydroxyphenyl)-1H-pyrrol-5-yl]benzenesulfonamide;
4-[1-(4-hydroxymethylphenyl)-1H-pyrrol-5-yl]benzenesulfonamide;

1-[4-(methylsulfonyl)phenyl]-5-(4-pyridyl)-1H-pyrrole;
1-[4-(methylsulfonyl)phenyl]-5-(3-pyridyl)-1H-pyrrole;
1-[4-(methylsulfonyl)phenyl]-5-(2-pyridyl)-1H-pyrrole;
1-[4-(methylsulfonyl)phenyl]-5-(4-methyl-2-pyridyl)-1H-pyrrole;
1-[4-(methylsulfonyl)phenyl]-5-(4-methyl-3-pyridyl)-1H-pyrrole;
1-[4-(methylsulfonyl)phenyl]-5-(5-methyl-2-pyridyl)-1H-pyrrole;
1- [4-(methylsulfonyl)phenyl)-5-(5-methyl-3-pyridyl)-1H-pyrrole;
1-[4-(methylsulfonyl)phenyl]-5-(3-methyl-2-pyridyl)-1H-pyrrole;
1-[4-(methylsulfonyl)phenyl]-5-(2-methyl-3-pyridyl)-1H-pyrrole;
5-(4-chlorophenyl)-1-[4-(methylsulfonyl)phenyl]-1H-pyrrole;
5-(4-methylthiophenyl)-1-[4-(methylsulfonyl)phenyl]-1H-pyrrole;
5-(4-methylsulfinylphenyl)-1-[4-(methylsulfonyl)phenyl]-1H-pyrrole;
5-(4-methoxyphenyl)-1-[4-(methylsulfonyl)phenyl]-1H-pyrrole;
5-(3-fluoro-4-methoxyphenyl)-1-[4-(methylsulfonyl)phenyl]-1H-pyrrole;
5-(3-chloro-4-methoxyphenyl)-1-[4-(methylsulfonyl)phenyl]-1H-pyrrole;
5-(3,5-dichloro-4-methoxyphenyl)-1-[4-(methylsulfonyl)phenyl]-1H-pyrrole;
5-(3,5-difluoro-4-methoxyphenyl)-1-[4-(methylsulfonyl)phenyl]-1H-pyrrole;
5-(3-chloro-4-fluorophenyl)-1-[4-(methylsulfonyl)phenyl]-1H-pyrrole;
5-(4-hydroxyphenyl)-1-[4-(methylsulfonyl)phenyl]-1H-pyrrole;
5-(4-hydroxymethylphenyl)-1-[4-(methylsulfonyl)phenyl]-1H-pyrrole;
5-[4-[1-[4-(aminosulfonyl)phenyl]-1H-pyrrol-1-yl]phenyl] ethanone;
4-[5-(cyclohexyl)-1H-pyrrol-1-yl]benzenesulfonamide;
4-[5-phenyl-1H-pyrrol-1-yl]benzenesulfonamide;
4-[5-(3,4-difluorophenyl)-1H-pyrrol-1-yl] benzenesulfonamide;
4-[5-(4-trifluoromethylphenyl)-1H-pyrrol-1-yl] benzenesulfonamide;
4-[5-(4-methylphenyl)-1H-pyrrol-1-yl] benzenesulfonamide;
4-[5-(4-pyridyl) -H-pyrrol-1-yl]benzenesulfonamide;
4-[5-(3-pyridyl)-1H-pyrrol-1-yl]benzenesulfonamide;
4-[5-(2-pyridyl)-1H-pyrrol-1-yl]benzenesulfonamide;
4-[5-(4-methyl-3-pyridyl ) -H-pyrrol- 1-yl] benzenesulfonamide;
4-[5-(4-methyl-2-pyridyl)-1H-pyrrol-1-yl] benzenesulfonamide;
4-[5-(5-methyl-3-pyridyl)-1H-pyrrol-1-yl] benzenesulfonamide;
4-[5-(5-methyl-2-pyridyl)-1H-pyrrol-1-yl] benzenesulfonamide;
4-[5-(2-methyl-3-pyridyl)-1H-pyrrol-1-yl] benzenesulfonamide;
4-[5-(3-methyl-2-pyridyl)-1H-pyrrol-1-yl] benzenesulfonamide;
4-[1-(4-fluorophenyl)-3-[(trifluoromethyl)sulfonyl]-1H-pyrrol-5-yl]benzenesulfonamide;
4-[3-bromo-1-(4-fluorophenyl)-1H-pyrrol-5-yl] benzenesulfonamide;
4-[3-chloro-1-(4-fluorophenyl)-1H-pyrrol-5-yl] benzenesulfonamide;
4-[1-(4-fluorophenyl)-3-trifluoromethyl-1H-pyrrol-5-yl] benzenesulfonamide;
4-[1-(4-fluorophenyl)-3-difluoromethyl-1H-pyrrol-5-yl] benzenesulfonamide;
2,2,2-trifluoro-1-[1-(4-fluorophenyl)-5-[4-(aminosulfonyl) phenyl]-1H-pyrrol-3-yl]ethanone;
4-[5-(4-chlorophenyl)-1H-pyrrol-1-yl]benzenesulfonamide;
4-[5-(4-methylthiophenyl)-1H-pyrrol-1-yl] benzenesulfonamide;
4-[5-(4-methylsulfinylphenyl)-1H-pyrrol-1-yl] benzenesulfonamide;
4-[5-(4-methoxyphenyl)-1H-pyrrol-1-yl] benzenesulfonamide;
4-[5-(3-fluoro-4-methoxyphenyl)-1H-pyrrol-1-yl] benzenesulfonamide;
4-[5-(3-chloro-4-methoxyphenyl)-1H-pyrrol-1-yl] benzenesulfonamide;
4-[5-(3,5-dichloro-4-methoxyphenyl)-1H-pyrrol-1-yl] benzenesulfonamide;
4-[5-(3-chloro-4-fluorophenyl)-1H-pyrrol-1-yl] benzenesulfonamide;
4-[5-(4-hydroxyphenyl)-1H-pyrrol-1-yl] benzenesulfonamide; and
4-[5-(4-hydroxymethylphenyl)-1H-pyrrol-1-yl] benzenesulfonamide.

The term "hydrido" denotes a single hydrogen atom (H). This hydrido radical may be attached, for example, to an oxygen atom to form a hydroxyl radical or two hydrido radicals may be attached to a carbon atom to form a methylene (—CH2—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. More preferred alkoxyalkyl radicals are "lower alkoxyalkyl" radicals having one to six carbon atoms and one or two alkoxy radicals. Examples of such radicals include methoxymethyl, methoxyethyl, ethoxyethyl, methoxybutyl and methoxypropyl. The "alkoxy" or "alkoxyalkyl" radicals may be further substituted with one or more halo atoms, such as fluoro, chloro or bromo, to provide "haloalkoxy" or haloalkoxyalkyl radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkenyl" embraces partially saturated carbocyclic radicals having three to twelve carbon atoms. More preferred cycloalkenyl radicals are "lower cycloalkenyl" radicals having three to about eight carbon atoms. Examples of such radicals include cyclobutenyl, cyclopentenyl and cyclohexenyl. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Said "aryl" group may have 1 to 3 substituents such as halo, lower alkyl, hydroxy, lower alkoxy, lower alkylcarbonyl and lower haloalkyl. The term "heterocyclyl" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms[e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated heterocyclic radicals. Examples of "heteroaryl" radicals include unsaturated 3 to 6 membered heteromonocyclic group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-bipyridazinyl, etc.], etc.; unsaturated 3 to 6-membered heteromonocyclic group containing an oxygen atom, for example, pyranyl, 2-furyl, 3-furyl, etc.; unsaturated 3 to 6-membered heteromonocyclic group containing a sulfur atom, for example, 2-thienyl, 3-thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4- thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclyl" group may have 1 to 3 substituents such as halo, lower alkyl, hydroxy, oxo, amino and lower alkylamino. More preferred heteroaryl radicals include five to six membered heteroaryl radicals. The term "heteroarylalkyl" embraces heteroaryl-substituted alkyl radicals. More preferred heteroarylalkyl radicals are "lower heteroarylalkyl" radicals having one to six carbon atoms and a heteroaryl radical. Examples include such heteroarylalkyl radicals such as pyridylmethyl and thienylmethyl. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces alkylthio radicals attached to an alkyl radical. More preferred alkylthioalkyl radicals are "lower alkylthioalkyl" radicals having alkyl radicals of one to six carbon atoms and an alkylthio radical as described above. Examples of such radicals include methylthiomethyl. The term "arylthio" embraces radicals containing an aryl radical, attached to a divalent sulfur atom, such as a phenylthio radical. The term "arylthioalkyl" embraces arylthio radicals attached to an alkyl radical. More preferred arylthioalkyl radicals are "lower arylthioalkyl" radicals having alkyl radicals of one to six carbon atoms and an arylthio radical as described above. Examples of such radicals include phenylthiomethyl. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide "haloalkylsulfonyl" radicals. More preferred haloalkylsulfonyl radicals are "lower haloalkylsulfonyl" radicals having one or more halo atoms attached to lower alkylsulfonyl radicals as described above. Examples of such lower haloalkylsulfonyl radicals include fluoromethylsulfonyl, trifluoromethylsulfonyl and chloromethylsulfonyl. The term "arylsulfonyl" embraces aryl radicals as defined above, attached to a sulfonyl radical.

Examples of such radicals include phenylsulfonyl. The terms "sulfamyl", "aminosulfonyl" and "sulfonamidyl" denotes $NH_2O_2S$—. The term "acyl" denotes a radical provided by the residue after removal of hydroxyl from an organic acid. Examples of such acyl radicals include formyl, alkanoyl and aroyl radicals. The terms "carboxy" or "carboxyl", whether used alone or with other terms, such as "carboxyalkyl", denotes —$CO_2H$. The term "carbonyl", whether used alone or with other terms, such as "alkoxycarbonyl", denotes —(S=O)—. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The aryl in said aralkyl may be additionally substituted with halo, alkyl, alkoxy, halkoalkyl and haloalkoxy. The terms benzyl and phenylmethyl are interchangeable. The terms "alkylcarbonyl", "arylcarbonyl" and aralkylcarbonyl" include radicals having alkyl, aryl and aralkyl radicals, respectively, as defined above, attached via an oxygen atom to a carbonyl radical. More preferred alkylcarbonyl radicals are "lower alkylcarbonyl" radicals having one to six carbon atoms. Examples of such radicals include methylcarbonyl and ethylcarbonyl. More preferred aralkylcarbonyl radicals are "lower aralkylcarbonyl" radicals having aryl radicals attached to alkyl radicals having one to six carbon atoms. Examples of such aralkylcarbonyl radicals include benzylcarbonyl. An example of an arylcarbonyl radical is phenylcarbonyl. The term "alkoxycarbonylalkyl" embraces radicals having "alkoxycarbonyl", as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl. The term "haloalkylcarbonyl" embraces radicals having a haloalkyl radical as described above attached to a carbonyl radical. More preferred radicals are "lower haloalkylcarbonyl" radicals where lower haloalkyl radicals, as described above are attached to a carbonyl radical. The term "carboxyalkyl" embraces radicals having a carboxy radical as defined above, attached to an alkyl radical. More preferred are "lower carboxyalkyl" which embrace lower alkyl radicals as defined above. Examples of such lower carboxyalkyl radicals include carboxymethyl, carboxyethyl, carboxypropyl and carboxybutyl. The term "heteroaralkyl" embraces heteroaryl-substituted alkyl radicals. More preferred heteroaralkyl radicals are "lower heteroaralkyl" radicals having five to six membered heteroaryl radicals attached to one to six carbon atoms. Examples of such radicals include pyridylmethyl, quinolylmethyl, thienylmethyl, furylethyl and quinolylethyl. The heteroaryl in said heteroaralkyl may be additionally substituted with halo, alkyl, alkoxy, halkoalkyl and haloalkoxy. The term "aryloxy" embraces aryl radicals, as defined above, attached to an oxygen atom. Examples of such radicals include phenoxy. Said "aryloxy" group may be optionally substituted with 1 to 3 substituents, such as halo, lower alkyl, hydroxy, lower alkoxy, lower alkylcarbonyl and lower haloalkyl. The term "heteroaryloxy" embraces heteroaryl radicals as defined above attached to an oxygen radical. More preferred heteroaryloxy radicals are "lower heteroaryloxy" radicals having five to six membered heteroaryl radicals. The term "aralkoxy" embraces oxy-containing aralkyl radicals attached through an oxygen atom to other radicals. The term "aralkoxyalkyl" embraces alkyl radicals having one or more aralkoxy radicals attached to the alkyl radical, that is, to form monoaralkyloxyalkyl and diaralkyloxyalkyl radicals. The "aralkoxy" or "aralkoxyalkyl" radicals may be further substituted on the aryl ring portion of the radical. More preferred aralkoxyalkyl radicals are "lower aralkoxyalkyl" having an alkoxy attached to one to six carbon atoms. Examples of lower aralkoxyalkyl radicals include benzyloxymethyl. The term "heteroarylthio" embraces radicals having heteroaryl radicals attached to a sulfur radical. More preferred heteroarylthio radicals are "lower heteroarylthio" radicals having five to six membered heteroaryl radicals. Examples of such radicals include 2-furylthio, 2-thienylthio, 3-thienylthio, 4-pyridylthio and 3-pyridylthio. The term "heteroarylalkylthio" denotes radicals having an heteroaryl radical attached to an alkylthio radical. More preferred heteroarylalkylthio radicals are "lower heteroarylalkylthio" radicals having heteroaryl radicals attached to lower alkylthio radicals as described above. Examples of such radicals include furylmethylthiomethyl and quinolylmethylthioethyl. The term "heteroarylalkylthioalkyl" denotes radicals having an heteroaryl radical attached to an alkylthio radical further attached through the sulfur atom to an alkyl radical. More preferred heteroarylalkylthioalkyl are "lower heteroarylalkylthioalkyl" radicals having lower heteroarylalkyl radicals as described above. Examples of such radicals include furylmethylthiomethyl and quinolylmethylthioethyl. The term "heteroarylthioalkyl" denotes radicals having an heteroaryl radical attached to a sulfur atom further attached through the sulfur atom to an alkyl radical. More preferred heteroarylthioalkyl radicals are "lower heteroarylthioalkyll, having lower heteroarylthio radicals as described above. Examples of such radicals include thienylthiomethyl and pyridylthiohexyl. The term "aralkylthio" embraces radicals having aralkyl radicals attached to a bridging sulfur atom. More preferred aralkylthio radicals are "lower aralkylthio" radicals having the aryl radicals attached to one to six carbon atoms. Examples of such radicals include benzylthio and phenylethylthio. The term "aralkylthioalkyl" embraces radicals having aralkyl radicals attached to alkyl radicals through a bridging sulfur atom. More preferred aralkylthioalkyl radicals are "lower aralkylthioalkyl" radicals having the aralkylthio radicals attached to one to six carbon atoms. Examples of such radicals include benzylthiomethyl and phenylethylthiomethyl. The term "heteroaryloxyalkyl" denotes radicals having an heteroaryl radical attached to an oxygen atom further attached through the oxygen atom to an alkyl radical. More preferred heteroaryloxyalkyl radicals are "lower heteroaryloxyalkyl" radicals having five to six membered heteroaryl radicals. Examples of such radicals include furyloxyethyl, pyridyloxymethyl and thienyloxyhexyl. The term "aminoalkyl" embraces alkyl radicals substituted with amino radicals. More preferred aminoalkyl radicals are "lower aminoalkyl" having one to six carbon atoms. Examples include aminomethyl, aminoethyl and aminobutyl. The term "alkylaminoalkyl" embraces aminoalkyl radicals having the nitrogen atom substituted with at least one alkyl radical. More preferred alkylaminoalkyl radicals are "lower alkylaminoalkyl" having one to six carbon atoms attached to a lower aminoalkyl radical as described above. More preferred alkylamino radicals are "lower alkylamino"

radicals having one or two alkyl radicals of one to six carbon atoms, attached to a nitrogen atom. The term "alkylamino" denotes amino groups which have been substituted with one or two alkyl radicals. Suitable "alkylamino" may be mono or dialkylamino such as N-methylamino, N-ethylamino, N,N-dimethylamino, N,N-diethylamino or the like. The term "alkylaminocarbonyl" embraces alkylamino radicals, as described above, to a carbonyl radical. More preferred alkylaminocarbonyl radicals are "lower alkylaminocarbonyl" having lower alkylamino radicals, as described above, attached to a carbonyl radical. Examples of such radicals include N-methylaminocarbonyl and N,N-dimethylcarbonyl. The term "arylamino" denotes amino groups which have been substituted with one or two aryl radicals, such as N-phenylamino. The "arylamino" radicals may be further substituted on the aryl ring portion of the radical. The terms "N-arylaminoalkyl" and "N-aryl-N-alkylaminoalkyl" denote amino groups which have been substituted with one aryl radical or one aryl and one alkyl radical, respectively, and having the amino group attached to an alkyl radical. More preferred arylaminoalkyl radicals are "lower arylaminoalkyl" having the arylamino radical attached to one to six carbon atoms. Examples of such radicals include N-phenylaminomethyl and N-phenyl-N-methylaminomethyl. The term "aminocarbonyl" denotes an amide group of the formula —C(=O)NH$_2$. The term "alkylaminocarbonylalkyl" denotes an alkylaminocarbonyl group which is attached to an alkyl radical. More preferred are "lower alkylaminocarbonylalkyl" having lower alkylaminocarbonyl radicals as described above attached to one to six carbon atoms. The term "aryloxyalkyl" embraces alkyl radicals having one or more aryloxy radicals, aryl radicals attached to a divalent oxygen atom, attached to the alkyl radical, that is, to form monoaryloxyalkyl and diaryloxyalkyl radicals. The more preferred aryloxyalkyl radicals are "lower aryloxyalkyl" radicals having aryloxy radicals attached to one to six carbon atoms. Examples include phenoxymethyl where the phenyl ring is optionally substituted with . The term "heteroarylalkoxy" embraces radicals having one or more heterocyclic radicals attached to an alkoxy radical. More preferred heteroarylalkoxy radicals are "lower heteroarylalkoxy" radicals having five to six membered heteroaryl radicals. Examples of such radicals include 2-, 3-thienylmethoxy, 2-, 3-furylmethoxy and 2-, 3-, 4-pyridylmethoxy. The term "heteroarylalkoxyalkyl" embraces alkyl radicals having one or more heterocyclic radicals attached to an alkoxy radical, further attached to the alkyl radical. More preferred heteroarylalkoxyalkyl radicals are "lower heteroarylalkoxyalkyl radicals having five to six membered heteroaryl radicals. Examples of such radicals include 2-thienylmethoxymethyl.

The present invention comprises a pharmaceutical composition comprising a therapeutically-effective amount of a compound of Formula I in association with at least one pharmaceutically-acceptable carrier, adjuvant or diluent.

The present invention also comprises a method of treating cyclooxygenase-2 mediated disorders, such as inflammation, in a subject, the method comprising treating the subject having such disorder with a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I-III may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic, methanesulfonic, ethanesulfonic, benzenesulfonic, pantothenic, stearic, toluenesulfonic, 2-hydroxyethanesulfonic, sulfanilic, cyclohexylaminosulfonic, algenic, β-hydroxybutyric, galactaric and galacturonic acid. Suitable pharmaceutically-acceptable base addition salts of compounds of Formulas I-III include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–VII, wherein the $R^1$–$R^8$ substituents are as defined for Formulas I-III, above, except where further noted.

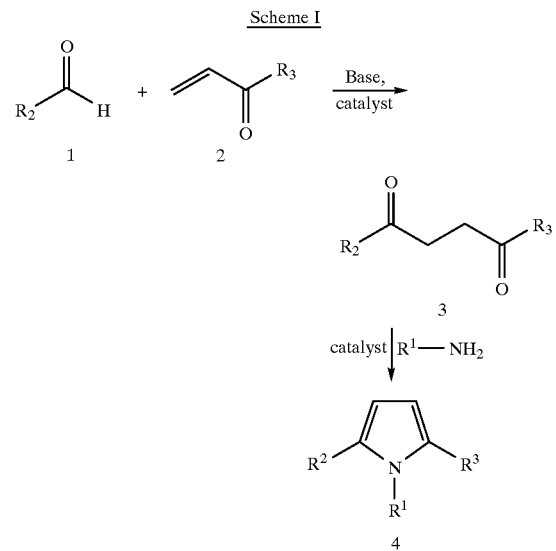

Scheme I

Scheme I shows the two-step general procedure for the synthesis of substituted pyrroles 4 of the invention. In step 1, aldehyde 1 is reacted with α,β-unsaturated ketones 2 in the presence of a base (such as triethylamine, diisopropylethylamine, pyridine and the like) to give the 1,4-diketone derivative 3. Suitable catalysts for this reaction are thiazolium salts or cyanides (e.g., NaCN, KCN). A variety of catalysts and conditions suitable for this reaction are discussed in *Angewandte Chemie* (Eng)., 15, 639 (1976) and the references cited therein. In step 2, the 1,4-diketone intermediate 3 is reacted with amines in the presence of acid catalysts such as p-toluenesulfonic acid to give the targeted pyrroles 4. Suitable solvents for this reaction are e. g., toluene, xylene and benzene, with or without the presence of molecular sieves.

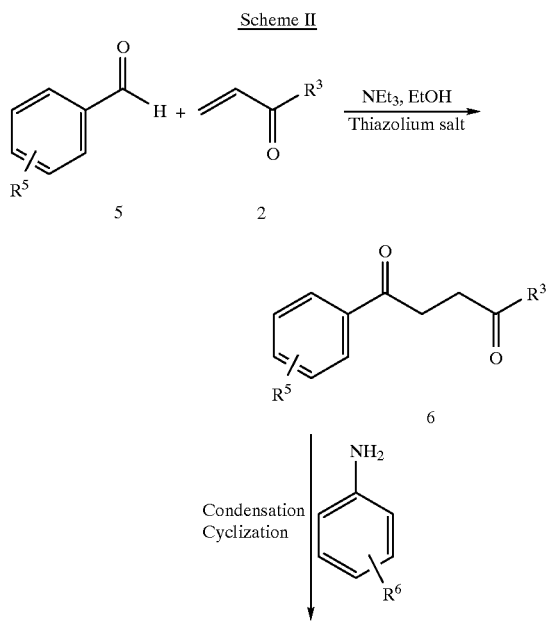

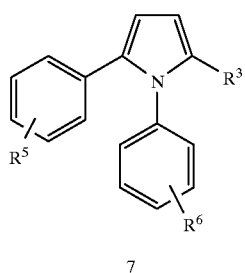

Scheme II shows the general procedure for the synthesis of 1,2-diphenylpyrroles 7 of the invention. In step 1, the substituted benzaldehyde 5 is reacted with α,β-unsaturated ketones 2 in the presence of a base to give the 1,4-diketone derivative 6. Suitable catalysts for this reaction are thiazolium salts or cyanides (e. g., NaCN, KCN). In step 2, the 1,4-diketone intermediate 6 is reacted with substituted anilines in the presence of acid catalysts such as p-toluenesulfonic acid to give the targeted 1,2-diphenylpyrroles 7.

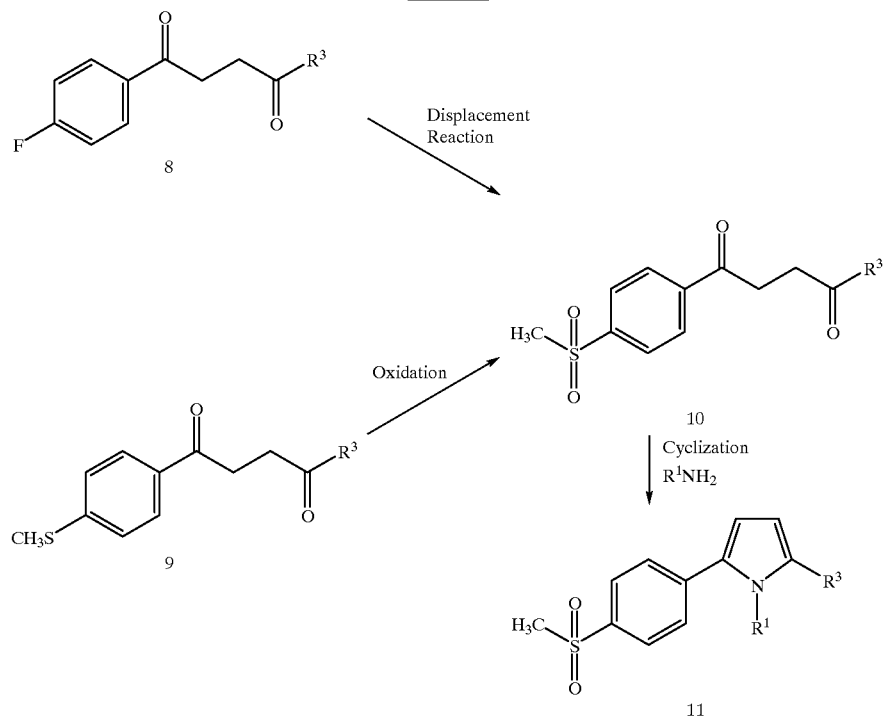

Scheme III shows synthesis of substituted pyrroles 11 containing a methylsulfonyl group. The synthesis of key intermediate 10 can be accomplished by direct displacement of a fluorine atom, such as with methanesulfinic acid sodium salt. Suitable solvents for this reaction are, e.g., dimethylformamide, dimethyl acetamide, dimethyl sulfoxide or 2-pyrrolidinone at temperature of about 100–140° C. for several hours to days. Alternately, the intermediate 10 can be synthesized by oxidation of the corresponding methylthio derivative 9. This oxidation may be carried with oxidizing agents such as OXONE® or hydrogen peroxide. The conversion of 10 to desired substituted pyrroles can be achieved by condensing with substituted amines 11 as discussed in step 2, Scheme I.

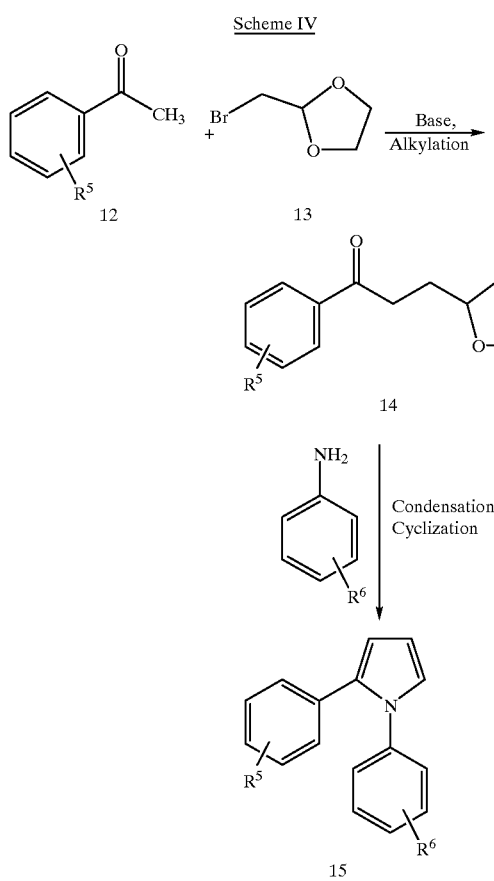

Scheme IV shows an alternative synthesis of 1,2-diphenylpyrroles 15 wherein $R^3$ is hydrido. In step 1, the substituted acetophenones 12 are reacted with 2-bromomethyl-1,3-dioxolane 13 to form the protected ketone 14 using a base such as NaH, KH, or potassium t-butoxide. Suitable solvents for this alkylation reaction include dimethylformamide, dimethylacetamide and dimethylsulfoxide. The reaction may be carried out at about −20° C. to about 50° C. In step 2, the desired 1,2-diphenylpyrroles 15 can be synthesized by condensing the protected ketone 14 with an aniline. The conditions used are similar to those discussed in step 2, Scheme I.

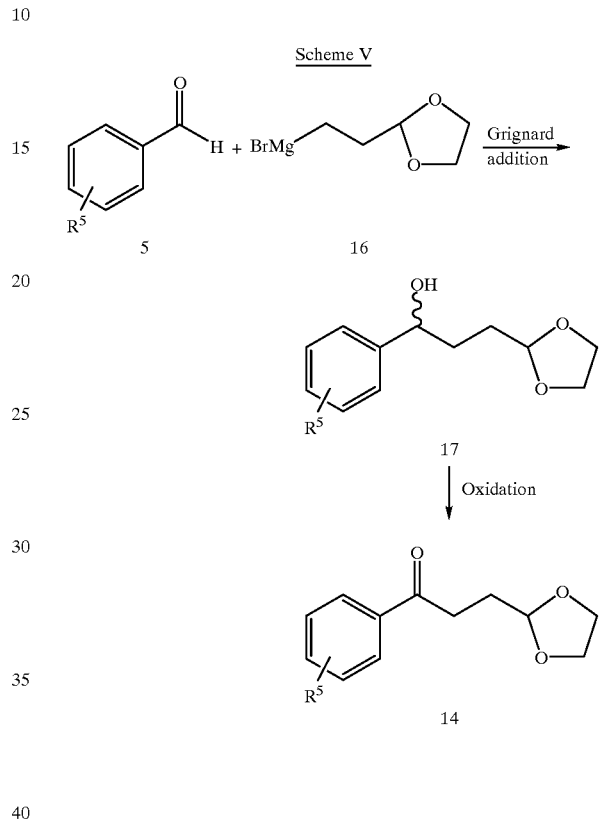

Scheme V shows an alternate method of synthesizing the intermediate 14 of Scheme IV. In step 1, the substituted benzaldehyde 5 is reacted with Grignard reagent from 3-bromoethyl-1,3-dioxolane 16 and magnesium to form the alcohol 17. This reaction is preferentially carried out in ethereal solvents such as tetrahydrofuran, diethyl ether, dioxane, dimethoxyethane at temperature of about −100–0° C. In step 2, the oxidation of the alcohol 17 to the desired ketone intermediate 14 can be carried out using a variety of conditions familiar to those skilled in the art.

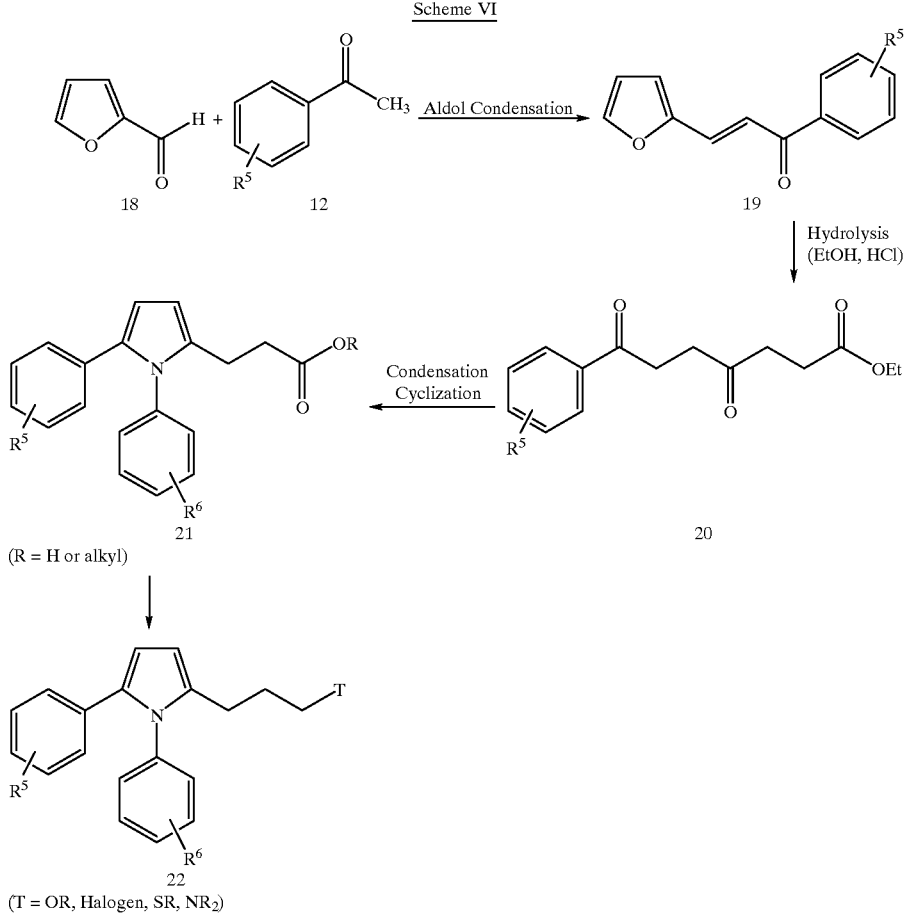

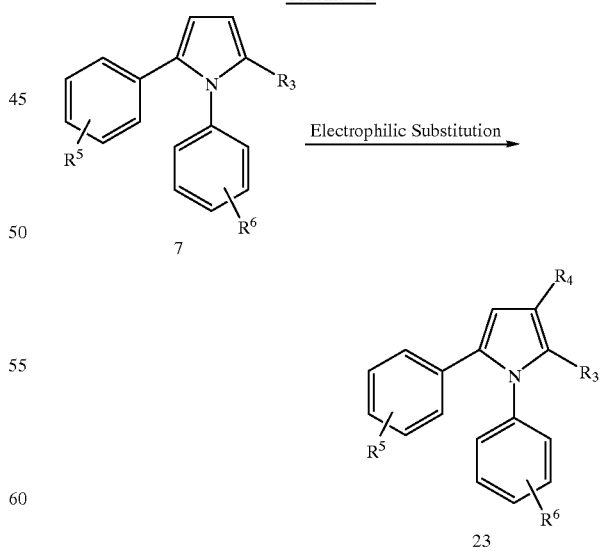

Scheme VI shows a general synthesis of 5 diarylpyrroles additionally substituted at position 2 of the pyrroles. In step 1, 2-furaldehyde 18 is condensed with substituted acetophenone 12 in the presence of a base to give the unsaturated intermediate 19. Suitable bases for this reaction are, e.g., sodium methoxide, 10 sodium (or potassium) L-butoxide, triethylamine, duisopropylethylamine and the like. In step 2, the furan ring is opened under hydrolytic conditions to give the intermediate 20. This reaction is preferably carried out in alcoholic solvents using aqueous mineral acids. In step 3, the intermediate 20 is reacted with substituted anilines to give the targeted pyrroles 21. This reaction can be carried out using the conditions suggested in step 2, Scheme 1. In step 4, the carboxylic group is reduced to the alcohol (22, T=OH) and the alcohol is converted to ether (22, T=OR) or other derivatives (22, T=halogen, $NR_2$, SR). These synthetic transformations can be achieved using the conditions familiar to those skilled in the art.

Scheme VII shows a general method for the synthesis of tetrasubstituted pyrroles 23 from trisubstituted pyrroles 7. A number of substituents such as ($R^4$=halogen, —CHO, —CN, —COR, —$SO_2R$, —$CO_2R$, alkyl, aralkyl, etc.) can be synthesized by direct electrophilic substitutions. For example, N-bromosuccinimide, N-chlorosuccinimide, iodine can be used for introduction of halogen substituted pyrroles. Dimethylformamide can be used for the synthesis of formyl ($R^4$=CHO) derivatives. The synthesis of acetyl (COR) or alkylsulfonyl ($SO_2R$) derivatives can be accomplished by using Friedel-Crafts reaction. The synthesis of compounds with variety of groups ($R^4$=halogen, alkyl, aminoalkyl, alkoxyalkyl, aryl, acyl and the like) can be accomplished by following the literature procedures (see, e.g., *J. Org. Chem* ., 55, 6317 (1990); *Eur. J. Med. Chem.*, 27, 701 (1992); *J. Org. Chem.*, 57, 1653 (1992); *J. Med. Chem.*, 35, 4813 (1992); and the references cited therein). Some of the targeted compounds (e.g., $R^4$=alkoxyalkyl, aminoalkyl, mercaptoalkyl, haloalkyl and the like) can also be synthesized by the functional group transformation of groups such as Br, CHO, $CO_2R$ using the conditions familiar to those skilled in the art.

The following examples contain detailed descriptions of the methods of preparation of compounds of Formula I-III. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures. In some cases, the assigned structures were confirmed by nuclear Overhauser effect (NOE) experiments.

The following abbreviations are used:

HCl—hydrochloric acid

HBr—hydrobromic acid

DMSO—dimethylsulfoxide $MgSO_4$—magnesium sulfate $Na_2SO_4$—sodium sulfate $H_2SO_4$—sulfuric acid AcOH—acetic acid DMF—dimethylformamide THF—tetrahydrofuran NaOH—sodium hydroxide Pt/C—platinum on carbon Pd/C—palladium on carbon EtOH—ethanol NaH—sodium hydride KH—potassium hydride NaCN—sodium cyanide KCN—potassium cyanide KBr—potassium bromide min—minutes h—hours OXONE®—potassium peroxymonosulfate

EXAMPLE 1

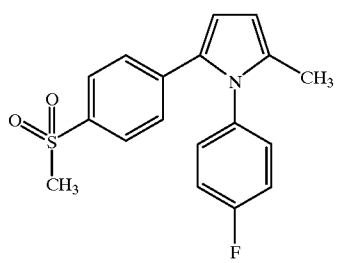

1-(4-Fluorophenyl)-2-methyl-5-[4-(methylsulfonyl) phenyl]-1H-pyrrole

Step 1: Preparation of 1-[4-(methylthio)phenyl]pentane-1,4-dione.

To a solution of 4-(methylthio)benzaldehyde (12 mL, 0.09 mol) in ethanol (30 mL), triethylamine (19.5 mL, 0.14 mol), methyl vinyl ketone (5.8 mL, 0.07 mol) and 3-ethyl-5-(2-hydroxyethyl)-4 methylthiazolium bromide (3.53 g, 0.014 mol) were added. The mixture was heated at 75–80° C. for 20 hours and cooled. The solvent was removed under reduced pressure and the residue was treated with 2N HCl (300 mL). After extraction with methylene chloride, the organic layer was washed with aqueous sodium bicarbonate and water. The organic fractions were dried over $MgSO_4$, filtered and concentrated to give a crude orange liquid (16.2 g). After chromatography on silica gel (hexane/ethyl acetate, 7/3), the desired compound was isolated as a pale yellow solid (12.3 g, 71%): mp (DSC) 75° C.; IR (KBr) 3410, 3030, 1711, 1680, 1591, 1556, 1491, 1427; MS (EI) 222 ($M^+$). Anal. Calc'd for $C_{12}H_{14}SO_2$: C, 64.84; H, 6.35. Found: C, 64.65; H, 6.33.

Step 2: Preparation of 1-(4-methylsulfonylphenyl)-1,4-pentanedione

To a solution of 1-(4-methylthiophenyl)-1,4-pentanedione (7.8 g, 35 mmol) in methanol (150 mL), Oxone® (37.7 g, 61.4 mmol) was dissolved in water (150 mL) and added over 5 minutes. After stirring at 25° C. for 2 hours, the reaction mixture was diluted with water (400 mL) and extracted with methylene chloride (3×400 mL). The organic layer was washed with brine (200 mL), water (200 mL) and dried ($MgSO_4$). After filtration and concentration, the crude material was purified by chromatography (silica gel, hexane/ethyl acetate, 3/1) to give 1-(4-methylsulfonylphenyl)-1,4-pentanedione (8.0 g, 91%) as a white crystalline compound: mp (DSC) 138° C.; IR (KBr) 3435, 3098, 3003, 1944, 1713, 1686, 1593, 1572, 1406; MS (DCI, $NH_3$-PCI) 255 ($MH^+$). Anal Calc'd. for $C_{12}H_{14}SO_4$: C, 56.68; H, 5.55. Found: C, 56.60; H, 5.78.

Step 3: Preparation of 1-(4-fluorophenyl)-2-methyl-5-[4-(methylsulfonyl)phenyl]-1H-pyrrole A mixture of 1-(4-methylsulfonylphenyl)-1,4-pentanedione (580 mg, 2.28 mmol) of Step 2, 4-fluoroaniline (0.24 ml, 2.5 mmol) and p-toluenesulfonic acid (30 mg) in toluene (50 ml) was heated to reflux for 20 hours. The reaction mixture was cooled, filtered and concentrated. The crude mixture (820 mg) was purified by chromatography (silica gel, hexane/ethyl acetate, 7/3) to give 1-(4-fluorophenyl)-2-methyl-5-[4-(methylsulfonyl) phenyl)-1H-pyrrole (595 mg, 79%) as a white solid: mp (DSC) 157° C. Anal Calc'd. for $C_{18}H_{16}NSO_2F$: C, 65.64; H, 4.90; N, 4.25; S, 9.73. Found: C, 65.44; H, 5.05; N, 4.16; S, 9.90.

EXAMPLE 2

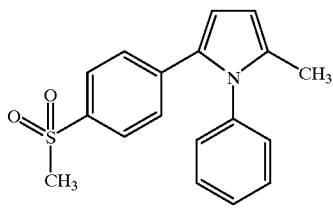

2-Methyl-5-[4-(methylsulfonyl)phenyl]-1-phenyl-1H-pyrrole

A mixture of 1-(4-methylsulfonylphenyl)-1,4-pentanedione (Example 1, step 2) (300 mg, 1.18 mmol), aniline (0.12 ml, 1.3 mmol) and p-toluenesulfonic acid (25 mg) in toluene (50 ml) was heated to reflux for 20 hours. The reaction mixture was cooled, filtered and concentrated. The crude brownish solid (420 mg) was purified by chromatography (silica gel, hexane/ethyl acetate, 7/3) to give 2-methyl-5-[4-(methylsulfonyl)phenyl]-1-phenyl-1H-pyrrole (305 mg, 83%) as a white solid: mp (DSC) 148° C. Anal Calc'd. for $C_{18}H_{17}NSO_2$: C, 69.43; H, 5.50; N, 4.50; S, 10.30. Found: C, 69.18; H, 5.42; N, 4.42; S, 10.06.

EXAMPLE 3

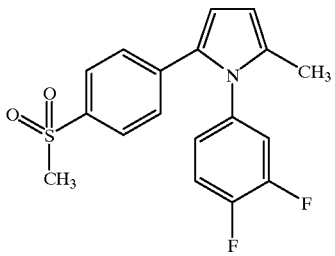

1-(3,4-Difluorophenyl)-2-methyl-5-[4-(methylsulfonyl)phenyl]-1H-pyrrole

A mixture of 1-(4-methylsulfonylphenyl)-1,4-pentanedione (Example 1, Step 2) (300 mg, 1.18 mmol), 3,4-difluoroaniline (0.13 ml, 1.3 mmol) and p-toluenesulfonic acid (25 mg) in toluene (80 ml) was heated to reflux for 24 hours. The reaction mixture was cooled, filtered and concentrated. The crude dark orange solid (700 mg) was purified by chromatography (silica gel, hexane/ethyl acetate, 7/3) to give 1-(3,4-difluorophenyl)-2-methyl-5-[4-(methylsulfonyl)phenyl]-1H-pyrrole (370 mg, 90%) as a white solid: mp (DSC) 151° C. Anal Calc'd. for $C_{18}H_{15}NSO_2F_2$: C, 62.24; H, 4.35; N, 4.03. Found: C, 62.08; H, 4.52; N, 4.05.

EXAMPLE 4

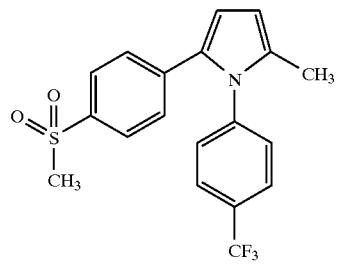

2-Methyl-5-[4-(methylsulfonyl)phenyl]-1-[4-(trifluoromethyl)phenyl]-1H-pyrrole

A mixture of 1-(4-methylsulfonylphenyl)-1,4-pentanedione (Example 1, Step 2) (300 mg, 1.18 mmol), 4-(trifluoromethyl)aniline hydrochloride (257 mg, 1.3 mmol) and p-toluenesulfonic acid (30 mg) in toluene (80 ml) was heated to reflux for 20 hours. The reaction mixture was cooled, filtered and concentrated. The crude solid (560 mg) was purified by chromatography (silica gel, hexane/ethyl acetate, 7/3) to give 2-methyl-5-[4-(methylsulfonyl)phenyl]-1-[4-(trifluoromethyl)phenyl]-1H-pyrrole (351 mg, 78%) as a white solid: mp (DSC) 130° C. Anal Calc'd. for $C_{19}H_{16}NSO_2F_3$: C, 60.15; H, 4.25; N, 3.69. Found: C, 60.38; H, 4.44; N, 3.67.

EXAMPLE 5

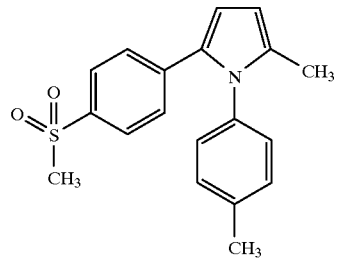

2-Methyl-1-(4-methylphenyl)-5-[4-(methylsulfonyl)phenyl]-1H-pyrrole

A mixture of 1-(4-methylsulfonylphenyl)-1,4-pentanedione (Example 1, Step 2) (335 mg, 1.32 mmol), p-toluidine (156 mg, 1.45 mmol) and p-toluenesulfonic acid (25 mg) in toluene (100 ml) was heated to reflux for 20 hours. The reaction mixture was cooled, filtered and concentrated. The crude solid (560 mg) was purified by chromatography (silica gel, hexane/ethyl acetate, 7/3) to give 2-methyl-1-(4-methylphenyl)-5-[4-(methylsulfonyl)phenyl]-1H-pyrrole (390 mg, 91%) as a white solid: mp (DSC) 144° C. Anal Calc'd. for $C_{19}H_{19}NSO_2$: C, 70.13; H, 5.88; N, 4.30; S, 9.85. Found: C, 69.99; H, 6.23; N, 4.18; S, 9.74.

EXAMPLE 6

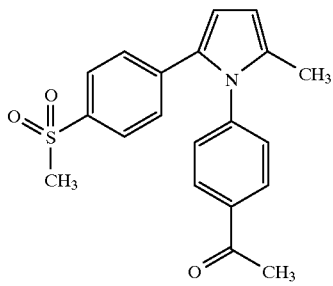

1-[4-[2-Methyl-5-[4-(methylsulfonyl)phenyl]-1H-pyrrol-1-yl]phenyl]ethanone

A mixture of 1-(4-methylsulfonylphenyl)-1,4-pentanedione (Example 1, Step 2) (400 mg, 1.57 mmol), p-amino-acetophenone (234 mg, 1.73 mmol) and p-toluenesulfonic acid (30 mg) in toluene (40 ml) was heated to reflux for 5 hours. The reaction mixture was cooled, filtered and concentrated. The crude reddish solid (1.2 g) was purified by chromatography (silica gel, hexane/ethyl acetate, 6/4) to give 1-[4-[2-methyl-5-[4-(methylsulfonyl)phenyl]-1H-pyrrol-1-yl]phenyl]ethanone (336 mg, 61%) as a white solid: mp 179–80° C. Anal Calc'd. for $C_{20}H_{19}NSO_3 \cdot 0.1\ H_2O$: C, 64.67; H, 5.70; N, 3.77; S, 8.63. Found: C, 64.68; H, 5.52; N, 3.82; S, 8.08.

EXAMPLE 7

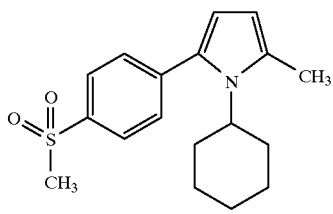

1-Cyclohexyl-2-methyl-5-[4-(methylsulfonyl)phenyl]-1H-pyrrole

A mixture of 1-(4-methylsulfonylphenyl)-1,4-pentanedione (Example 1, Step 2) (820 mg, 3.23 mmol), cyclohexylamine (410>1, 3.55 mmol) and p-toluenesulfonic acid (50 mg) in toluene (75 ml) was heated to reflux for 24 hours. The reaction mixture was cooled, filtered and concentrated. The crude solid (1.14 g) was purified by chromatography (silica gel, hexane/ethyl acetate, 1/1) to give 1-cyclohexyl-2-methyl-5-[4-(methylsulfonyl)phenyl]-1H-pyrrole (350 mg, p6%) as a white solid: mp (DSC) 141 ° C. Anal Calc'd. for $C_{18}H_{23}NSO_2$: C, 68.10; H, 7.30; N, 4.41; S, 10.10. Found: C, 68.22; H, 7.25; N, 4.30; S, 10.16.

EXAMPLE 8

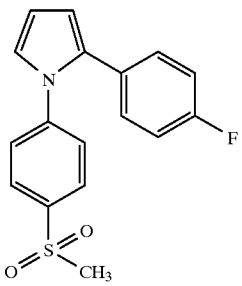

2-(4-Fluorophenyl)--1-[4-(methylsulfonyl)phenyl]-1H-pyrrole

Step 1: Preparation of α-(4-fluorophenyl)-1,3-dioxolane-2-propan-3-ol

A solution of 2-(2-bromoethyl)-1,3-dioxolane (1.76 ml, 15 mmol) in THF (10 ml) was added over 10 minutes to a suspension of magnesium turnings (410 mg, 16.5 mmol) in THF (10 ml). After stirring for 20 minutes, the reaction mixture was cooled to −70° C. and a solution of 4-fluorobenzaldehyde (1.07 ml, 10 mmol) in THF (10 ml) was added over 10 minutes. The reaction mixture was stirred at −70° C. for 2 hours and quenched with aqueous ammonium chloride. The reaction solution was warmed to room temperature and extracted with ethyl acetate. The organic layer was washed with brine, dried ($MgSO_4$), filtered and concentrated. The crude was obtained as a white liquid (2.54 g) and purified by chromatography (silica gel, hexane/ethyl acetate, 7/3) to give α-(4-fluorophenyl)-1,3-dioxolane-2-propan-3-ol as a white oil (1.88 g, 83%): Anal Calc'd. for $C_{12}H_{15}FO_3 \cdot 0.2\ HO$: C, 62.71; H, 6.75. Found: C, 62.73; H, 6.64.

Step 2: Preparation of 3-(1,3-dioxolan-2-yl)-1-(4-fluorophenyl)propan-1-one

To a solution of α-(4-fluorophenyl)-1,3-dioxolane-2-propan-3-ol (Step 1) (1.75 g, 7.74 mmol) in methylene chloride (100 ml), pyridinium chlorochromate (2.5 g, 11.6 mmol) was added. After stirring at room temperature for 3 hours, the mixture was diluted with ether and filtered through a short silica gel column. The column was eluted with ether and the fractions were combined and concentrated to give the ketone as a white solid (1.69 g, 96%): mp (DSC) 143° C. Anal Calc'd. for $C_{12}H_{13}FO_3$: C, 64.28; H, 5.84. Found: C, 64.85; H, 6.05.

Step 3: Preparation of 2-(4-fluoroThenyl)-1-[4-(methylsulfonyl)phenyl]-1H-pyrrole A mixture of the ketone (Step 2) (448 mg, 2 mmol), 4-(methylsulfonyl)aniline (380 mg, 2.2 mmol) and p-toluenesulfonic acid (30 mg) in toluene (40 ml) was heated to reflux for 18 hours. The reaction was cooled, filtered and concentrated. The crude solid (750 mg) was purified by chromatography (silica gel, hexane/ethyl acetate, 1/1) to give 2-(4-fluorophenyl)-1-[4-(methylsulfonyl)phenyl]-1H-pyrrole (310 mg, 55%) as a white solid: mp (DSC) 201° C. Anal Calc'd. for $C_{17}H_{14}NSFO_2 \cdot 0.2\ H_2O$: C, 64.01; H, 4.55; N, 4.39; S, 10.05. Found: C, 64.18; H, 4.33; N, 4.32; S, 10.36.

EXAMPLE 9

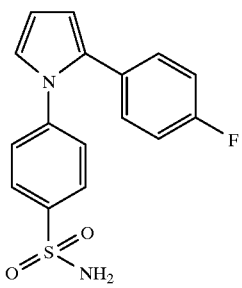

4-[2-(4-Fluorophenyl)-1H-pyrrol-1-yl] benzenesulfonamide

A mixture of 3-(1,3-dioxolan-2-yl)-1-(4-fluorophenyl)propan-1-one (Example 8, Step 2) (1.6 g, 7.14 mmol), sulfanilamide (1.35 g, 7.86 mmol), p-toluenesulfonic acid (120 mg) and molecular sieves (4 Å, 3 g) in toluene (250 ml) was heated to reflux for 98 hours. The reaction was cooled, filtered and concentrated. The crude brownish solid (3.2 g) was purified by chromatography (silica gel, hexane/ethyl acetate, 6/4) to give 4-[2-(4-fluorophenyl)-1H-pyrrol-1-yl] benzenesulfonamide (920 mg, 40%) as a white solid: mp (DSC) 206° C. Anal Calc'd. for $C_{16}H_{13}N_2SFO_2 \cdot 0.2\ H_2O$: C, 60.06; H, 4.22; N, 8.76; S, 10.02. Found: C, 60.13; H, 4.21; N, 8.61; S, 10.15.

EXAMPLE 10

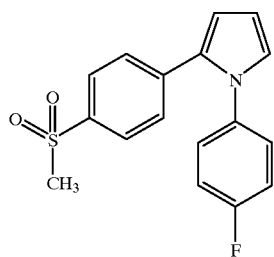

1-(4-Fluorophenyl)-2-[4-(methylsulfonyl)phenyl]-1H-pyrrole

Step 1: Preparation of 5,5-dimethyl-1,3-dioxane-2-propan-3-ol 5,5-Dimethyl-1,3-dioxane-2-propan-3-ol was synthesized by following the literature procedure [J. Org. Chem., 57, 2195 (1992)].

Step 2: Preparation of 5,5-dimethyl-1,3-dioxane-2-propanal

To a cold solution of oxalyl chloride (5.5 ml, 63.2 mmol) in methylene chloride (25 ml) at -78° C., DMSO (10.2 ml, 0.14 mol) was injected in over 5 minutes. After stirring for 15 minutes, a solution of 5,5-dimethyl-1,3-dioxane-2-propan-3-ol (Step 1) (10 g, 57.5 mmol) in methylene chloride (100 ml) was added. The reaction solution was stirred for 1 hour and triethylamine (40 ml, 0.2 mol) was added. After stirring at -70° C. for 1 hour, the reaction mixture was warmed to room temperature and stirred for 2 hours. The reaction was quenched with water and extracted with methylene chloride. The organic fractions were washed with aqueous sodium bicarbonate and brine. After drying ($Na_2SO_4$), filtration and concentration, the crude was purified by chromatography (silica gel, hexane/ethyl acetate, 7/3) to give 5,5-dimethyl-1,3-dioxane-2-propanal (6.1 g, 61%) as a colorless liquid: Anal Calc'd. for $C_9H_{16}O_3 \cdot 0.2\ H_2O$: C, 61.48; H, 9.40. Found: C, 61.46; H, 9.24.

Step 3: Preparation of 3-(5.5-dimethyl-1,3-dioxan-2-yl)-1-(4-fluorophenyl)propan-1-ol To a cold solution of 5,5-dimethyl-1,3-dioxane-2-propanal (2 g, 11.62 mmol) (Step 2) at -70° C. in THF (50 ml), 4-fluorophenyl magnesium bromide (8.7 ml, 2M solution in ether, 17.44 mmol) was added. After stirring at -70° C. for 2 hours, the mixture was warmed to room temperature and stirred overnight. The reaction was quenched with water and extracted with ethyl acetate. The organic fractions were combined and washed successively with water and brine. After drying ($MgSO_4$), filtration and concentration, the crude compound (3.5 g) was purified by chromatography to give 3-(5,5-dimethyl-1,3-dioxan-2-yl)-1-(4-fluorophenyl) propan-1-ol (2.73 g) as a white solid: mp (DSC) 84° C. Anal Calc'd. for $C_{15}H_{21}FO_3$: C, 67.14; H, 7.89. Found: C, 67.18; H, 7.98.

Step 4: Preparation of 3-(5.5-dimethyl-1,3-dioxan-2-yl)-1-(4-fluorophenyl)pro-an-1-one To a solution of 3-(5,5-dimethyl-1,3-dioxan-2-yl)-1-(4-fluorophenyl)propan-1-ol (Step 3) (2.6 g, 10.7 mmol) in methylene chloride (100 ml), pyridinium chlorochromate (3.5 g, 16.05 mmol) was added. After stirring at room temperature for 3 hours, the reaction mixture was diluted with ether and filtered through a short silica gel column. The column was eluted with ether and the fractions containing the ketone were combined and concentrated (2.2 g, 85%): mp (DSC) 65° C. Anal Calc'd. for $C_{15}H_{19}FO_3$: C, 67.65; H, 7.19. Found: C, 67.21; H, 7.43.

Step 5: Preparation of 3-(5.5-dimethyl-1,3-dioxan-2-yl)-1-[4-(methylsulfonyl)phenyl]propan-1-one To a solution of 3-(5,5-dimethyl-1,3-dioxan-2-yl)-1-(4-fluorophenyl)propan-1-one (Step 4) (1.68 g, 6.3 mmol) in dimethylformamide (75 ml), methanesulfinic acid sodium salt (2.9 g, 28.4 mmol) was added. The reaction mixture was heated at 120-30° C. for 72 hours. After cooling, the solvent was removed under reduced pressure and the reaction mixture was diluted with water. The material was extracted with methylene chloride and washed with brine. After drying ($MgSO_4$), filtration and concentration, the crude solid (2.78 g) was purified by chromatography (silica gel, hexane/ethyl acetate, 6/4) to give the sulfone (1.62 g, 79%) as a white solid: mp (DSC) 104° C. Anal Calc'd. for $C_{16}H_{22}SO_5$: C, 58.88; H, 6.79; S, 9.82. Found: C, 58.76; H, 7.01; S, 10.21.

Step 6: Preparation of 1-(4-fluorophenyl)-2-[4-(methylsulfonyl)-phenyl]-1H-pyrrole A mixture of 3-(5,5-dimethyl-1,3-dioxan-2-yl)-1-[4-(methylsulfonyl)phenyl]propan-1-one (Step 5), (1.6 g, 4.9 mmol), 4-fluoroaniline (510 μl, 5.4 mmol) and p-toluenesulfonic acid (120 mg) in toluene (200 ml) was heated to reflux for 72 hours. The reaction mixture was cooled, filtered and concentrated. The crude solid (2.48 g) was purified by chromatography (silica gel, hexane/ethyl acetate, 6/4) to give 1-[4-fluorophenyl)-2-[4-(methylsulfonyl)phenyl]-1H-pyrrole (695 mg, 45%) as a white solid: mp (DSC) 163° C. Anal Calc'd. for $C_{17}H_{14}NSFO_2$: C, 64.75; H, 4.47; N, 4.44. Found: C, 64.71; H, 4.53; N, 4.43.

EXAMPLE 11

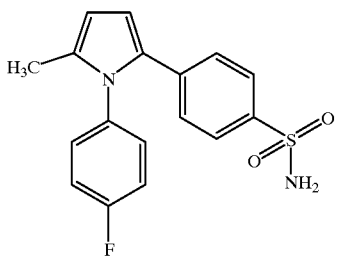

4-[1-(4-Fluorophenyl)-5-methyl-1H-pyrrol-2-yl]
benzenesulfonamide

Step 1: Preparation of 4-(aminosulfonyl)benzoic acid To a solution of 4-(chlorosulfonyl)benzoic acid (25 g, 0.11 mol) in ether (1.2 L), ammonium hydroxide (36 ml) was added. After stirring at room temperature for 5 hours, the solvent was removed and the residue was stirred with 3N HCl (1 L) for 80 minutes and filtered. The solid obtained was washed with water (2×20 ml) and with ether (3×20 ml), and dried under reduced pressure at 80° C. After concentration, the white solid obtained (22 g, 97%) was used in the next step without further purification: mp 279–81° C. Anal Calc'd. for $C_7H_7NSO_4$: C, 41.79; H, 3.51; N, 6.46; S, 15.99. Found: C, 41.90; H, 3.45; N, 6.98; S, 15.75.

Step 2: Preparation of methyl [4-(aminosulfonyl)]benzoate

To a solution of 4-(aminosulfonyl)benzoic acid (16 g, 79.6 mmol) (Step 1) in methanol (600 ml), conc. $H_2SO_4$ (1.2 ml) was added and the mixture was heated at reflux for 4 days. The solvent was removed and washed with ether. The white solid (16.5 g, 96%) was used in the next reaction without further purification.

Step 3: Preparation of 4-(hydroxymethyl) benzenesulfonamide

To a solution of methyl [4-(aminosulfonyl)]benzoate (5.8 g, 27 mmol) (Step 2) in THF (400 ml), methanol (1.6 ml, 40 mmol) and lithium borohydride (20 ml, 2M solution in THF, 42 mmol) were added over 10 minutes. After heating at reflux for 3.5 hours, the reaction mixture was cooled and poured over ice containing 1N HCl (80 ml). The reaction mixture was extracted with ethyl acetate, dried ($Na_2SO_4$), filtered and concentrated. The crude mixture was purified by chromatography (silica gel, hexane/ethyl acetate, 1/1) to give 4-(hydroxymethyl)benzenesulfonamide (3.8 g, 75%) as a white solid.

Step 4: Preparation of 4-(formyl)benzenesulfonamide

To a solution of 4-(hydroxymethyl)benzenesulfonamide (Step 3) (3.75 g, 20 mmol) in a mixture of acetone (250 ml) and methylene chloride (250 ml), pyridinium chlorochromate (6.47 g, 30 mmol) was added. After stirring at room temperature for 5 hours, the reaction mixture was diluted with ether and filtered through a short silica gel column. The column was eluted with hexane/ethyl acetate, (1/1). The fractions containing the desired material were combined and concentrated to give a white solid (2.0 g, 53%): mp 104–106° C. Anal Calc'd. for $C_7H_7NSO_3$: C, 45.40; H, 3.81; N, 7.56; S, 17.31. Found: C, 45.61; H, 3.59; N, 7.18; S, 16.27.

Step 5: Preparation of 47(1,3-dioxopentyl) benzenesulfonamide

To a solution of 4-(formyl)benzenesulfonamide (Step 4) (900 mg, 4.8 mol) in DMF (10 ml), sodium cyanide (23.5 mg, 0.48 mmol) in DMF (20 ml) was added. After stirring for 5 minutes, a solution of methyl vinyl ketone (0.4 ml, 4.8 mmol) in DMF (15 ml) was added. After stirring at room temperature for 20 hours, the reaction mixture was diluted with water and extracted with methylene chloride. The organic fractions were combined, washed with brine, dried ($Na_2SO_4$), filtered and concentrated. The crude was purified by chromatography on silica gel (hexane/ethyl acetate, 3/1) to give the desired compound as a white solid (180 mg, 15%).

Step 6: Preparation of 4-[1-[4-fluorophenyl)-5-methyl-1H-pyrrol-2-yl]benzenesulfonamide A mixture of 4-(1,3-dioxopentyl)benzenesulfonamide (160 mg, 0.63 mmol) of (Step 5), 4-fluoroaniline (65 µl, 0.69 mmol) and p-toluenesulfonic acid (6.7 mg) in toluene (25 ml) was heated at reflux for 20 hours. The reaction mixture was cooled, filtered and concentrated. The crude mixture (820 mg) was purified by chromatography (silica gel, toluene/ethyl acetate, 8/2) to give 4-[1-(4-fluorophenyl)-5-methyl-1H-pyrrol-2-yl]benzenesulfonamide (92 mg, 45%) as a white solid: mp 147–48° C. Anal Calc'd. for $C_{17}H_{15}N_2FSO_2$: C, 61.14; H, 4.65; N, 8.39; S, 9.60. Found: C, 61.34; H, 4.70; N, 8.21; S, 9.63.

EXAMPLE 12

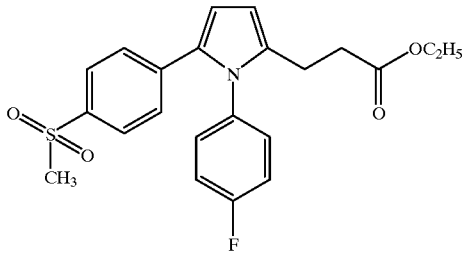

Ethyl 1-(4-fluorophenyl)-5-[4-(methylsulfonyl)
phenyl]-1H-pyrrole-2-propanoate

Step 1: Preparation of 1-(4-fluorophenyl)-3-(2-furanyl) propan-1-one

To a solution of 2-furaldehyde (4.15 ml, 50 mmol) and 4-fluoroacetophenone (6.16 ml, 50 mmol) in methanol (200 ml), sodium methoxide (2.85 g, 50 mmol) was added. After stirring at room temperature for 18 hours, the reaction mixture was concentrated, resuspended in ethyl acetate (600 ml) and diluted with water. The organic layer was separated, washed with brine, dried ($MgSO_4$), filtered and concentrated. The crude solid (10.27 g) was purified by chromatography (silica gel, hexane/ethyl acetate, 7/3) to give 1-(4-fluorophenyl)-3-(2-furanyl)propan-1-one (8.9 g, 95%) as a white solid: mp (DSC) 72° C. Anal Calc'd. for $C_{13}H_{10}FO$: C, 72.22; H, 4.20. Found: C, 72.18; H, 4.38.

Step 2: Preparation of ethyl 4-fluoro-$\gamma,\zeta$-dioxobenzeneheltanoate

A solution of ethyl 1-(4-fluorophenyl)-3-(2-furanyl) propan-1-one (Step 1) (7.2 g, 33.3 mmol) in ethanol (200 ml) and conc. HCl (40 ml) was heated at 80–85° C. for 72 hours. The solvent was removed under reduced pressure and redissolved in methylene chloride. The organic layer was separated and concentrated to give a black solid (16.8 g). Chromatography (silica gel, hex/ethyl acetate, 1/1) gave ethyl 4-fluoro-$\gamma,\zeta$-dioxobenzeneheptanoate (3.9 g, 41%) as a white solid: mp (DSC) 73° C. Anal Calc'd. for $C_{15}H_{17}FO_4$: C, 64.28; H, 6.11. Found: C, 64.50; H, 5.89. 1

Step 3: Preparation of ethyl 4-(methylsulfonyl)-$\gamma,\zeta$-dioxobenzeneheptanoate To a solution of ethyl 4-fluoro-$\gamma,\zeta$-dioxobenzeneheptanoate (Step 2) (870 mg, 3.1 mmol) in DMF (25 ml), methanesulfinic acid sodium (1.27 g, 12.4 mmol) was added. The reaction mixture was heated at 130–35° C. for 30 hours. After cooling, the solvent was removed under reduced pressure and the reaction mixture was diluted with water. The material was extracted with ethyl acetate and washed with brine. After drying (MgSO$_4$), filtration and concentration, the crude dark brown solid (840 mg) was purified by chromatography (silica gel, hexane/ethyl acetate, 1/1) to give the sulfone (270 mg, 26%) as a white solid: mp (DSC) 97° C. Anal Calc'd. for C$_{16}$H$_{20}$SO$_6$: C, 56.46; H, 5.92; S, 9.42. Found: C, 56.56; H, 6.10; S, 9.62.

Step 4: Preparation of ethyl 1-(4-fluorophenyl)-5-[4-(methylsulfonyl)phenyl]-1H-pyrrole-2-propanoate A mixture of ethyl 4-(methylsulfonyl)-γ,ζ-dioxobenzeneheptanoate (Step 3), (270 mg, 0.79 mmol), 4-fluoroaniline (83 μl, 0.87 mmol) and p-toluenesulfonic acid (25 mg) in toluene (40 ml) was heated at reflux for 24 hours. The reaction mixture was cooled, filtered and concentrated. The crude solid (360 mg) was purified by chromatography (silica gel, hexane/ethyl acetate, 1/1) to give ethyl 1-(4-fluorophenyl)-5-[4-(methylsulfonyl)phenyl]-1H-pyrrole-2-propanoate (246 mg, 75%) as a white solid: mp (DSC) 134° C. Anal Calc'd. for C$_{22}$H$_{22}$NSFO$_4$: C, 63.60; H, 5.34; N, 3.37; S, 7.72. Found: C, 63.29; H, 5.51; N, 3.38; S, 8.05.

EXAMPLE 13

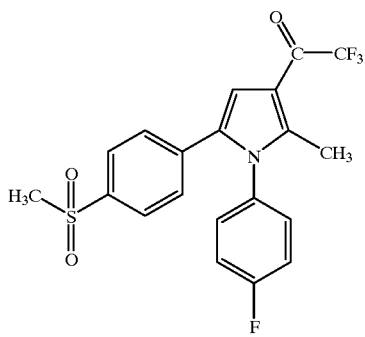

2,2,2-Trifluoro-1-[1-(4-fluorophenyl)-2-methyl-5-[4-(methylsulfonyl)phenyl]-1H-pyrrol-3-yl]ethanone To a solution of 1-(4-fluorophenyl)-2-methyl-5-[4-(methylsulfonyl)phenyl]-1H-pyrrole (Example 1) (800 mg, 2.43 mmol) in trifluoroacetic acid (7 ml), trifluoroacetic anhydride (0.7 ml, 4.86 mmol) was added and the mixture was heated at 50° C. for 3 hours. The reaction mixture was poured over ice and neutralized with dilute ammonium hydroxide to pH ~9. After extraction with ethyl acetate, the organic layer was washed successively with water and brine. The organic fractions were dried (MgSO$_4$), filtered and concentrated. The pale yellow crude solid (1.02 g) was purified by chromatography (silica gel, hexane/ethyl acetate, 7/3) to give 2,2,2-trifluoro-1-[1-(4-fluorophenyl)-2-methyl-5-[4-(methylsulfonyl)phenyl]-1H-pyrrol-3-yl]ethanone (800 mg, 77%) as a white solid: mp (DSC) 196° C. Anal Calc'd. for C$_{20}$H$_{15}$NSF$_4$O$_3$·0.5 H$_2$O: C, 55.30; H, 3.71; N, 3.22. Found: C, 55.55, H, 3.79; N, 3.20.

EXAMPLE 14

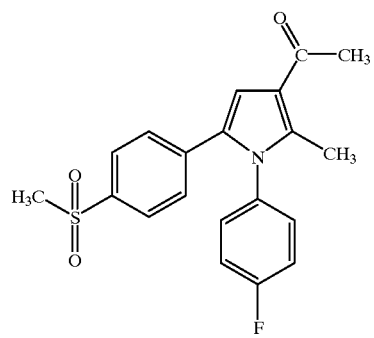

1-[1-(4-Fluorophenyl)-2-methyl-5-[4-(methylsulfonyl)phenyl]-1H-pyrrol-3-yl]ethanone Acetyl chloride (120 41, 1.67 mmol) was slowly added to a stirred slurry of aluminum chloride (223 mg, 1.67 mmol) in methylene chloride (15 ml) at −5° C. After 30 minutes, a solution 1-(4-fluorophenyl)-2-methyl-5-[4-(methylsulfonyl)phenyl]-1H-pyrrole (Example 1) (500 mg, 1.52 mmol) in methylene chloride (20 ml) was added. The reaction mixture was warmed to room temperature and stirred for 18 hours. The reaction mixture was poured over ice-water and extracted with methylene chloride. The organic fraction was washed with brine, dried (MgSO$_4$), filtered and concentrated. The crude yellowish solid (570 mg) was purified by chromatography (silica gel, hexane/ethyl acetate, 6/4) to give 1-[1-(4-fluorophenyl)-2-methyl-5-[4-(methylsulfonyl)phenyl]-1H-pyrrol-3-yl]ethanone (170 mg, 30%) as a white solid: mp (DSC) 211° C. Anal Calc'd. for C$_{20}$H$_{18}$NSFO$_3$·0.25 H$_2$O: C, 63.90; H, 4.96; N, 3.75. Found: C, 63.96; H, 5.04; N, 3.65.

EXAMPLE 15

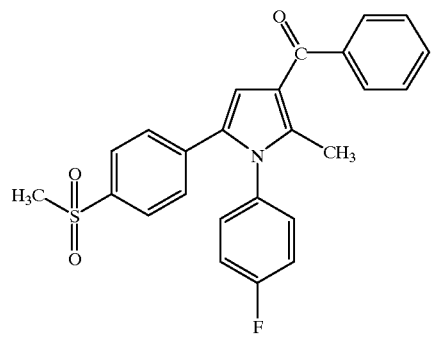

[1-(4-Fluorophenyl)-2-methyl-5-[4-(methylsulfonyl)phenyl-1H-pyrrol-3-yl]-phenylmethanone Benzoyl chloride (180 μl, 1.52 mmol) was slowly added to a stirred slurry of aluminum chloride (223 mg, 1.67 mmol) in methylene chloride (15 ml) at −10° C. After 30 minutes, a solution of 1-(4-fluorophenyl)-2-methyl-5-[4-(methylsulfonyl)phenyl]-1H-pyrrole (Example 1) (500 mg, 1.52 mmol) in methylene chloride (10 ml) was added. The reaction mixture was warmed to room temperature and stirred for 20 hours. The reaction mixture was poured over ice-water and extracted with methylene chloride. The organic fraction was washed with brine, dried (MgSO$_4$), filtered and concentrated. The crude yellowish solid (570 mg) was purified by chromatography (silica gel, hexane/ethyl acetate, 6/4) to give [1-(4-fluorophenyl)-2-methyl-5-[4-(methylsulfonyl)phenyl]-1H-pyrrol-3-yl]phenylmethanone (54 mg, 8%) as a white solid: Anal Calc'd. for $C_{25}H_{20}NSFO_3 \cdot 0.5\ H_2O$: C, 67.86; H, 4.78; N, 3.17. Found: C, 67.59; H, 4.70; N, 3.07.

EXAMPLE 16

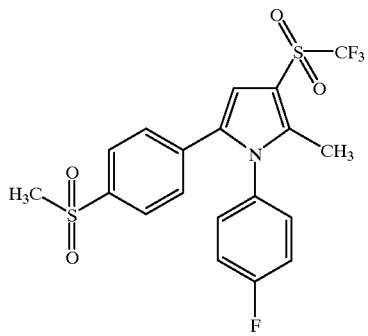

1-(4-Fluorophenyl)-2-methyl-5-[4-(methylsulfonyl)phenyl]-3-[(trifluoromethyl)sulfonyl]-1H-pyrrole To a solution of 1-(4-fluorophenyl)-2-methyl-5-[4-(methylsulfonyl)phenyl]-1H-pyrrole (Example 1) (2.5 g, 7.6 mmol) in methylene chloride (100 ml) at 0° C., aluminum chloride (1.15 g, 8.36 mmol) and trifluoromethanesulfonic anhydride (2 ml, 11.8 mmol) were added. After 30 minutes, the reaction mixture was warmed to room temperature and heated at reflux for 48 hours. The reddish orange reaction mixture was cooled, poured over ice-water and extracted with methylene chloride. The organic fractions were washed with brine, dried (MgSO$_4$), filtered and concentrated. The crude orange solid (3.2 g) was purified by chromatography (silica gel, hexane/ethyl acetate, 7/3) to give 1-(4-fluorophenyl)-2-methyl-5-[4-(methylsulfonyl)phenyl]-3-[(trifluoromethyl)sulfonyl]-1H-pyrrole (248 mg, 7%) as a white solid: mp 162–64° C. Anal Calc'd. for $C_{19}H_{15}NS_2F_4O_4$: C, 49.45; H, 3.28; N, 3.04. Found: C, 49.46; H, 3.34; N, 2.95.

EXAMPLE 17

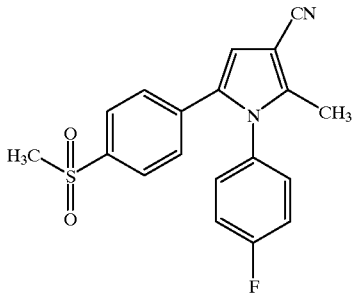

1-(4-Fluorophenyl)-2-methyl-5-[4-(methylsulfonyl)phenyl]-1H-pyrrole-3-carbonitrile To a cold solution of 1-(4-fluorophenyl)-2-methyl-5-[4-(methylsulfonyl)phenyl]-1H-pyrrole (Example 1) (750 mg, 2.28 mmol) in DMF (8 ml) and acetonitrile (8 ml) at –78° C., chlorosulfonyl isocyanate (200 μl, 2.28 mmol) was added. The reaction mixture was warmed to 20° C. over 4 hours, quenched by adding excess of water, and extracted with ethyl acetate. The organic fractions were washed with brine, dried (MgSO$_4$), filtered and concentrated. The crude colorless liquid (0.77 g) was purified by chromatography (silica gel, hexane/ethyl acetate, 6/4) to give 1-(4-fluorophenyl)-2-methyl-5-[4-(methylsulfonyl)phenyl]-1H-pyrrole-3-carbonitrile (620 mg, 77%) as a white solid: mp (DSC) 205° C. Anal Calc'd. for $C_{19}H_{15}N_2SFO_2$: C, 64.39; H, 4.27; N, 7.90. Found: C, 64.11; H, 4.45; N, 7.60.

EXAMPLE 18

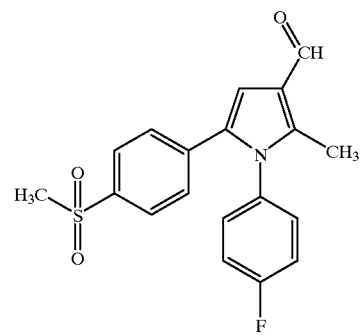

1-(4-Fluorophenyl)-2-methyl-5-[4-(methylsulfonyl)phenyl]-1H-pyrrole-3-carboxaldehyde To a solution of 1-(4-fluorophenyl)-2-methyl-5-[4-(methylsulfonyl)phenyl]-1H-pyrrole (Example 1) (1.55 g, 4.71 mmol) in dimethylformamide (3.65 ml, 47 mmol) and toluene (20 ml), phosphorous oxychloride (3.5 ml, 37.7 mmol) was added. After stirring for 20 minutes, the reaction mixture was heated at 70° C. for 5 hours. The reaction mixture was cooled, poured into aqueous sodium acetate solution and extracted with ethyl acetate. The organic fractions were washed with 10% aqueous potassium carbonate and water. After drying (Na$_2$SO$_4$), filtration and concentration, the crude yellowish liquid (2.06 g) was purified by chromatography (silica gel, hexane/ethyl acetate, 6/4) to give 1-(4-fluorophenyl)-2-methyl-5-[4-(methylsulfonyl)phenyl]-1H-pyrrole-3-carboxaldehyde (1.2 g, 71%): mp (DSC) 155° C. Anal Calc'd. for $C_{19}H_{16}NSFO_3$: C, 63.85; H, 4.51; N, 3.92. Found: C, 63.50; H, 4.66; N, 3.85.

EXAMPLE 19

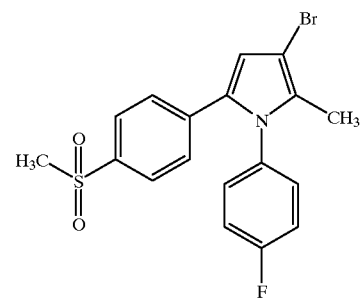

3-Bromo-1-(4-fluorophenyl)-2-methyl-5-[4-(methylsulfonyl)phenyl]-1H-pyrrole

To a solution of 1-(4-fluorophenyl)-2-methyl-5-[4-(methylsulfonyl)phenyl]-1H-pyrrole (Example 1) (3.3 g, 10 mmol) in THF (80 ml) at −70° C., N-bromosuccinimide (1.78 g, 10 mmol) was added over 10 minutes. The reaction was warmed to 20° C. over 3 hours and stirred for 18 hours. After dilution with aqueous sodium bicarbonate, the mixture was extracted with ethyl acetate. The organic fractions were washed with water, dried (MgSO$_4$), filtered and concentrated. The crude yellowish liquid (4.52 g) was purified by chromatography (silica gel, hexane/ethyl acetate, 7/3) to give 3-bromo-1-(4-fluorophenyl)-2-methyl-5-[4-(methylsulfonyl)phenyl]-1H-pyrrole (3.6 g, 88%): mp (DSC) 153° C. Anal Calc'd. for $C_{18}H_{15}NSBrFO_2$: C, 52.95; H, 3.70; N, 3.43; S, 19.53. Found: C, 53.01; H, 3.93; N, 3.39; S, 19.06.

EXAMPLE 20

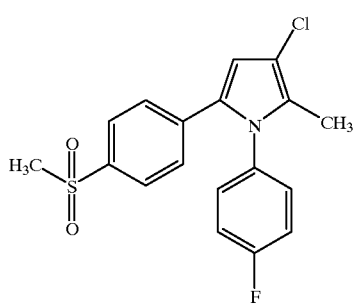

3-Chloro-1-(4-fluorophenyl)-2-methyl-5-[-4-(methylsulfonyl)phenyl]-1H-pyrrole

To a solution of 1-(4-fluorophenyl)-2-methyl-5-[4-(methylsulfonyl)phenyl]-1H-pyrrole (Example 1) (1 g, 3.03 mmol) in THF (100 ml) at −70° C., N-chlorosuccinimide (488 mg, 3.65 mmol) was added over 10 minutes. The reaction mixture was warmed to 20° C. over 3 hours and stirred for 18 hours. More N-chlorosuccinimide (450 mg, 3.37 mmol) was added and the mixture was stirred for 6 hours. After dilution with aqueous potassium carbonate, the reaction mixture was extracted with ethyl acetate. The organic fractions were washed with water, dried (MgSO$_4$), filtered and concentrated. The crude dark orange solid (1.3 g) was purified by chromatography (silica gel, hexane/ethyl acetate, 1/1) to give 3-chloro-1-(4-fluorophenyl)-2-methyl-5-[-4-(methylsulfonyl)phenyl]-1H-pyrrole (107 mg, 10%): mp (DSC) 172° C. Anal Calc'd. for $C_{18}H_{15}NSClFO_2$: C, 59.42; H, 4.16; N, 3.85. Found: C, 59.21; H, 4.10; N, 3.56.

EXAMPLE 21

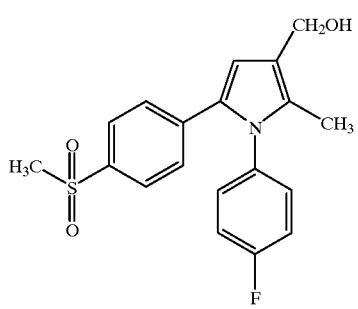

1-(4-Fluorophenyl)-2-methyl-5-[4-(methylsulfonyl)phenyl]-1H-pyrrole-3-methanol

To a solution of 1-(4-fluorophenyl)-2-methyl-5-[4-(methylsulfonyl)phenyl]-1H-pyrrole-3-carboxaldehyde (Example 18) (1.4 g, 3.9 mmol) in EtOH (30 ml), sodium borohydride (297 mg, 7.84 mmol) was added. After heating at reflux for 3 hours, the reaction mixture was cooled to room temperature and quenched with acetic acid. The solvent was removed under reduced pressure and the residue was redissolved in methylene chloride. After washing with 1N HCl and brine, the organic fractions were filtered, concentrated and purified by chromatography (silica gel, hexane/ethyl acetate, 1/1) to give 1-(4-fluorophenyl)-2-methyl-5-[4-(methylsulfonyl)phenyl]-1H-pyrrole-3-methanol (1.4 g, 100%) as a white solid: mp (DSC) 148° C. Anal Calc'd. for $C_{19}H_{18}NSFO_3 \cdot 0.4 H_2O$: C, 62.25; H, 5.17; N, 3.82; S, 8.75. Found: C, 62.29; H, 4.87; N, 3.86; S, 8.86.

EXAMPLE 22

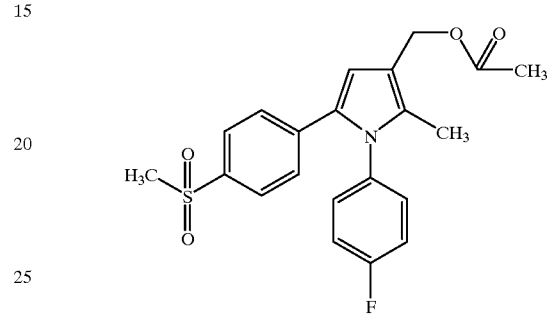

[1-(4-Fluorophenyl)-2-methyl-5-[4-(methylsulfonyl)phenyl]-1H-pyrrol-3-yl]methyl acetate To a solution of 1-(4-fluorophenyl)-2-methyl-5-[4-(methylsulfonyl)phenyl]-1H-pyrrole (Example 1) (500 mg, 2.87 mmol) in AcOH (5 ml), formaldehyde (0.22 ml, 40% solution in water, 2.87 mmol) was added. After heating at 50–55° C. for 90 minutes, the reaction mixture was cooled and poured over ice. The solution was made alkaline with 2N NaOH and extracted with methylene chloride. The organic fractions were washed with water and with brine, dried (MgSO$_4$), filtered and concentrated to give the crude product (780 mg) as a yellowish liquid. Chromatography (silica gel, hexane/ethyl acetate, 6/4) gave [1-(4-fluorophenyl)-2-methyl-5-[4-(methylsulfonyl)phenyl]-1H-pyrrol-3-yl]methyl acetate (250 mg, 22%) as a white solid: mp (DSC) 151° C. Anal Calc'd. for $C_{21}H_{20}NSFO_4$: C, 62.83; H, 5.02; N, 3.49. Found: C, 62.48; H, 5.16; N, 3.37.

EXAMPLE 23

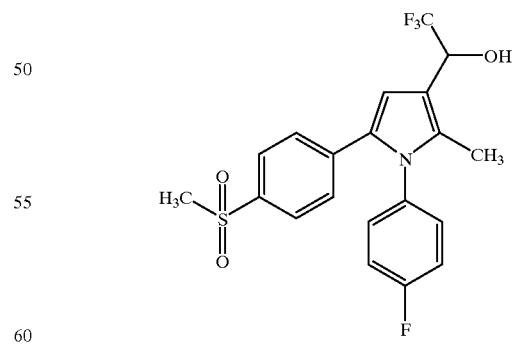

1-(4-Fluorophenyl) -2-methyl-5-[4-(methylsulfonyl)phenyl] -α,α,α-(trifluoromethyl) -1H-pyrrole-3-methanol To a solution of 2,2,2-trifluoro-1-[1-(4-fluorophenyl)-2-methyl-5-[4-(methylsulfonyl)phenyl]-1H-pyrrol-3-yl]

ethanone (Example 13) (310 mg, 0.73 mmol) in ethanol (10 ml) and acetic acid (10 ml), 4% Pd/C (51 mg) was added. The system was sealed, purged with nitrogen (5 times), with hydrogen (5 times) and then pressurized to 5 psi hydrogen. After for 24 hours, the system was vented, purged with nitrogen and filtered. The filtrate was concentrated and the crude (325 mg) was purified by chromatography (silica gel, hexane/ethyl acetate, 6/4) to give 1-(4-fluorophenyl)-2-methyl-5-[4-(methylsulfonyl)phenyl]-α,α,α-(trifluoromethyl)-1H-pyrrole-3-methanol (270 mg, 87%): mp (DSC) 213° C. Anal Calc'd. for $C_{20}H_{17}NSF_4O_3$: C, 56.20; H, 4.01; N, 3.28. Found: C, 56.07; H, 4.08; N, 3.19.

EXAMPLE 24

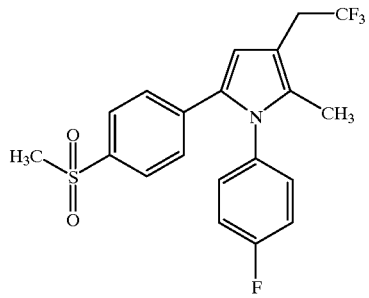

1-(4-Fluorophenyl)-2-methyl-5-[4-(methylsulfonyl)phenyl]-3-(2,2,2-trifluoroethyl)-1H-pyrrole To a solution of 1-(4-fluorophenyl)-2-methyl-5-[4-(methylsulfonyl)phenyl]-α,α,α-(trifluoromethyl)-1H-pyrrole-3-methanol (Example 23) (325 mg, 0.76 mmol) in trifluoroacetic acid (5 ml) and acetic acid (10 ml), 5% Pt/C (325 mg) was added. The system was sealed, purged with nitrogen (5 times), with hydrogen (5 times) and then pressurized to 60 psi hydrogen. After 48 hours, the system was vented, purged with nitrogen and filtered. The filtrate was concentrated, the residue was redissolved in methylene chloride and washed with aqueous potassium carbonate and brine. After drying ($MgSO_4$), filtration and concentration, the crude (320 mg) was purified by chromatography (silica gel, hexane/ethyl acetate, 7/3) to give 1-(4-fluorophenyl)-2-methyl-5-[4-(methylsulfonyl)phenyl]-3-(2,2,2-trifluoroethyl)-1H-pyrrole (135 mg, 43%): mp (DSC) 151° C. Anal Calc'd. for $C_{20}H_{17}NSF_4O_2 \cdot 0.25\ H_2O$: C, 57.76; H, 4.24; N, 3.37. Found: C, 57.73; H, 4.34; N, 3.30.

EXAMPLE 25

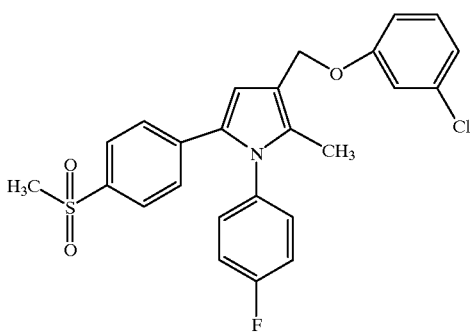

3-[(3-Chlorophenoxy)methyl]-1-(4-fluorophenyl)-2-methyl-5-[4-(methylsulfonyl)phenyl]-1H-pyrrole To a solution of 1-(4-fluorophenyl)-2-methyl-5-[4-(methylsulfonyl)phenyl]-1H-pyrrole-3-methanol (Example 21) (300 mg, 0.83 mmol), 3-chlorophenol (88 µl, 0.83 mmol), and triphenylphosphine (219 mg, 0.83 mmol) in THF (20 ml), diethyl azodicarboxylate (132 l, 0.83 mmol) was added. The mixture was stirred at room temperature for 48 hours. The solvent was removed under reduced pressure and the crude liquid (820 mg) was purified by chromatography (silica gel, hexane/ethyl acetate, 7/3) to give 3-[(3-chlorophenoxy)methyl]-1-(4-fluorophenyl)-2-methyl-5-[4-(methylsulfonyl)phenyl]-1H-pyrrole (75 mg, 19%): mp (DSC) 139° C. Anal Calc'd. for $C_{25}H_{21}NSClFO_3$: C, 63.89; H, 4.50; N, 2.98. Found: C, 63.85; H, 4.98; N, 2.76.

EXAMPLE 26

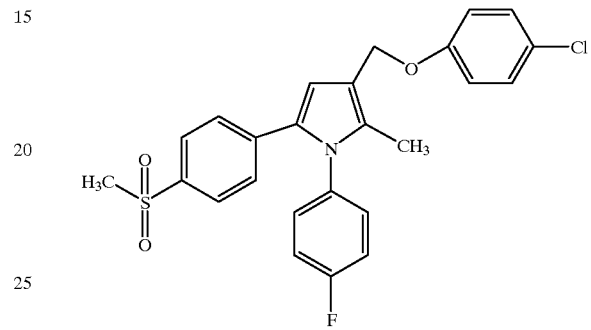

3-[(4-Chlorophenoxy)methyl]-1-(4-fluorophenyl)-2-methyl-5-[4-(methylsulfonyl)phenyl]-1H-pyrrole To a solution of 1-(4-fluorophenyl)-2-methyl-5-[4-(methylsulfonyl)phenyl]-1H-pyrrole-3-methanol (Example 21) (300 mg, 0.83 mmol), 4-chlorophenol (107 mg, 0.83 mmol), and triphenylphosphine (219 mg, 0.83 mmol) in THF (20 ml), diethyl azodicarboxylate (132 µl, 0.83 mmol) was added. The mixture was stirred at room temperature for 48 hours. The solvent was removed under reduced pressure and the crude (830 mg) was purified by chromatography (silica gel, hexane/ethyl acetate, 1/1) to give 3-[(4-chlorophenoxy)methyl]-1-(4-fluorophenyl)-2-methyl-5-[4-(methylsulfonyl)phenyl]-1H-pyrrole (29 mg, 7%): mp (DSC) 145° C. Anal Calc'd. for $C_{25}H_{21}NSClFO_3 \cdot 0.25\ H_2O$: C, 63.29; H, 4.57; N, 2.95. Found: C, 63.46; H, 4.57; N, 2.81.

BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory*

*Models for Testing NSAIDs*, in Non-steroidal Anti-Inflammatory Drugs, (J. Lombardino, ed. 1985)). The % inhibition shows the % decrease from control paw volume determined in this procedure and the data for selected compounds in this invention are summarized in Table I.

TABLE I

| Example | RAT PAW EDEMA<br>% Inhibition<br>@ 30mg/kg body weight | ANALGESIA<br>% Inhibition<br>@ 30mg/kg body weight |
|---|---|---|
| 8 | 56 | 47 |

Evaluation of COX-1 and COX-2 activity in vitro

The compounds of this invention exhibited inhibition in vitro of COX-2. The COX-2 inhibition activity of the compounds of this invention illustrated in the Examples was determined by the following methods.

a. Preparation of recombinant COX baculoviruses

Recombinant COX-1 and COX-2 were prepared as described by Gierse et al, [*J. Biochem.*, 305, 479–84 (1995)]. A 2.0 kb fragment containing the coding region of either human or murine COX-1 or human or murine COX-2 was cloned into a BamH1 site of the baculovirus transfer vector pVL1393 (Invitrogen) to generate the baculovirus transfer vectors for COX-1 and COX-2 in a manner similar to the method of D. R. O'Reilly et al (*Baculovirus Expression Vectors: A Laboratory Manual* (1992)). Recombinant baculoviruses were isolated by transfecting 4 µg of baculovirus transfer vector DNA into SF9 insect cells ($2 \times 10^8$) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer ($10^{7-10^8}$ pfu/mL) stocks of virus were prepared. For large scale production, SF9 insect cells were infected in 10 liter fermentors ($0.5 \times 10^6$/mL) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX-1 and COX-2 activity

COX activity was assayed as $PGE_2$ formed/pg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 µl of reaction mix into 160 µl ELISA buffer and 25 µM indomethacin. The $PGE_2$ formed was measured by standard ELISA technology (Cayman Chemical). Results are shown in Table II.

TABLE II

| Example | COX-2<br>IC50 µM | COX-1<br>IC50 µM |
|---|---|---|
| 1 | <0.1 | >100 |
| 2 | 0.2 | >100 |
| 3 | 0.3 | >100 |
| 4 | <0.1 | >100 |
| 5 | <0.1 | >100 |
| 6 | 2.9 | >100 |
| 7 | 0.5 | 62.4 |
| 8 | 0.5 | >100 |
| 9 | 0.3 | 10.4 |
| 10 | 10.2 | >100 |
| 11 | <0.1 | 3.8 |
| 13 | 0.1 | >10 |
| 14 | 1.6 | >100 |
| 15 | 1.0 | >30 |
| 16 | <0.1 | >100 |
| 17 | 0.8 | >100 |
| 18 | 3.2 | >100 |
| 19 | <0.1 | 0.8 |
| 20 | <0.1 | 4.5 |
| 21 | 3.9 | >100 |
| 22 | 0.5 | >100 |
| 23 | 1.4 | >100 |
| 24 | 0.1 | >100 |
| 25 | <0.1 | >100 |
| 26 | <0.1 | >100 |

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly, intraperitoneally, subcutaneously, intramuscularly or topically.

The phrase "co-therapy" (or "combination-therapy"), in defining use of a cyclooxygenase-2 inhibitor agent and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

The phrase "therapeutically-effective" is intended to qualify the amount of each agent which will achieve the goal of improvement in disease severity and the frequency of incidence over treatment of each agent by itself, while avoiding adverse side effects typically associated with alternative therapies.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

In the case of psoriasis and other skin conditions, it may be preferable to apply a topical preparation of compounds of this invention to the affected area two to four times a day.

For inflammations of the eye or other external tissues, e.g., mouth and skin, the formulations are preferably applied as a topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

All mentioned references are incorporated by reference as if here written.

Although this invention has been described with respect to specific embodiments, the details of these embodiments are not to be construed as limitations.

What is claimed is:

1. A compound of Formula I

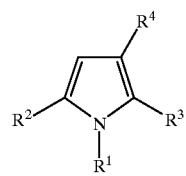

I wherein $R^1$ and $R^2$ are independently selected from aryl, cycloalkyl, cycloalkenyl and heterocyclyl, wherein $R^1$ and $R^2$ are optionally substituted at a substitutable position with one or more radicals independently selected from alkylsulfonyl, aminosulfonyl, haloalkylsulfonyl, halo, alkylthio, alkylsulfinyl, alkyl, cyano, carboxyl, alkoxycarbonyl, haloalkyl, hydroxyl, alkoxy, hydroxyalkyl, alkoxyalkyl, alkylcarbonyl, haloalkoxy, amino, alkylamino, arylamino and nitro;

wherein R³ is a radical selected from hydrido, halo, methyl and alkoxycarbonylalkyl; and wherein R⁴ is a radical selected from hydrido, halo, alkyl, haloalkyl, cyano, alkoxycarbonyl, carboxyl, formyl, aryl, heteroaryl, alkylsulfonyl, haloalkylsulfonyl, hydroxyalkyl, alkoxyalkyl, alkylcarbonyl, carboxyalkyl, alkoxycarbonylalkyl, alkylcarbonyloxyalkyl, mercaptoalkyl, alkylthioalkyl, haloalkylcarbonyl, haloalkyl(hydroxy)alkyl, aminoalkyl, alkylaminoalkyl and alkoxy;

provided at least one of R¹ and R² is phenyl substituted with methylsulfonyl or aminosulfonyl; and further provided R³ is hydrido when R¹ is phenyl substituted with aminosulfonyl or methylsulfonyl;

or a pharmaceutically-acceptable salt thereof.

2. Compound of claim 1 wherein R¹ and R² are independently selected from phenyl, lower cycloalkyl, lower cycloalkenyl and 5- or 6-membered heteroaryl, wherein R¹ and R² are optionally substituted at a substitutable position with one or more radicals independently selected from lower alkylsulfonyl, aminosulfonyl, lower haloalkylsulfonyl, halo, lower alkylthio, lower alkyl, cyano, carboxyl, lower alkoxycarbonyl, lower alkylcarbonyl, lower haloalkyl, hydroxyl, lower alkoxy, lower hydroxyalkyl, lower alkoxyalkyl, lower haloalkoxy, amino, lower alkylamino, arylamino and nitro; wherein R³ is a radical selected from hydrido, halo, methyl and lower alkoxycarbonylalkyl; and wherein R⁴ is a radical selected from hydrido, halo, lower alkyl, lower haloalkyl, cyano, lower alkoxycarbonyl, carboxyl, formyl, phenyl, 5- or 6-membered heteroaryl, lower alkylsulfonyl, lower haloalkylsulfonyl, lower hydroxyalkyl, lower alkoxyalkyl, lower alkylcarbonyl, lower carboxyalkyl, lower alkoxycarbonylalkyl, lower alkylcarbonyloxyalkyl, lower mercaptoalkyl, lower alkylthioalkyl, lower haloalkylcarbonyl, lower haloalkyl (hydroxy)alkyl, lower aminoalkyl, lower alkylaminoalkyl and lower alkoxy; or a pharmaceutically-acceptable salt thereof.

3. Compound of claim 2 wherein R¹ and R² are independently selected from phenyl, cyclohexyl, cyclohexenyl, benzofuryl, benzodioxolyl, furyl, imidazolyl, thienyl, thiazolyl, pyrrolyl, oxazolyl, isoxazolyl, triazolyl, pyrimidinyl, isoquinolyl, quinolinyl, benzimidazolyl, indolyl, pyrazolyl and pyridyl, wherein R¹ and R² are optionally substituted at a substitutable position with one or more radicals independently selected from methylsulfonyl, aminosulfonyl, fluoromethylsulfonyl, difluoromethylsulfonyl, fluoro, chloro, bromo, methylthio, methyl, ethyl, isopropyl, tert-butyl, isobutyl, pentyl, hexyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, methylcarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl, hydroxyethyl, methoxymethyl, ethoxymethyl, trifluoromethoxy, amino, methylamino, N,N-dimethylamino, phenylamino and nitro; wherein R³ is a radical selected from hydrido, fluoro, chloro, bromo, methyl, ethoxycarbonylethyl, and methoxycarbonylmethyl; and wherein R⁴ is a radical selected from hydrido, fluoro, chloro, bromo, methyl, ethyl, fluoromethyl, difluoromethyl, trifluoromethyl, cyano, methoxycarbonyl, ethoxycarbonyl, tert-butoxycarbonyl, carboxyl, formyl, phenyl, methylsulfonyl, trifluoromethylsulfonyl, hydroxymethyl, hydroxyethyl, methoxymethyl, ethoxymethyl, methylcarbonyl, ethylcarbonyl, trifluoromethylcarbonyl, trifluoro(hydroxy)ethyl, methoxycarbonylmethyl, ethoxycarbonylethyl, carboxymethyl, carboxypropyl, methylcarbonyloxymethyl, thienyl, furyl, and pyridyl, wherein the thienyl, furyl, pyridyl and phenyl radicals are optionally substituted at a substitutable position with one or more radicals selected from fluoro, chloro, bromo, methylthio, methylsulfinyl, methyl, ethyl, isopropyl, tert-butyl, isobutyl, pentyl, hexyl, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl, hydroxyethyl and trifluoromethoxy; or a pharmaceutically-acceptable salt thereof.

4. Compound of claim 1 selected from compounds, and their pharmaceutically acceptable salts, of the group consisting of 1-(4-fluorophenyl)-2-methyl-5-[4-(methylsulfonyl)phenyl]-1H-pyrrole;

2-methyl-5-[4-(methylsulfonyl)phenyl]-1-phenyl-1H-pyrrole;

1-(3,4-difluorophenyl)-2-methyl-5-[4-(methylsulfonyl)phenyl]-1H-pyrrole;

2-methyl-5-[4-(methylsulfonyl)phenyl]-1-[4-(trifluoromethyl)phenyl]-1H-pyrrole;

2-methyl-1-(4-methylphenyl)-5-[4-(methylsulfonyl)phenyl]-1H-pyrrole;

1-[4-[2-methyl-5-[4-(methylsulfonyl)phenyl]-1H-pyrrol-1-yl]phenyl]ethanone;

1-cyclohexyl-2-methyl-5-[4-(methylsulfonyl)phenyl]-1H-pyrrole;

2-(4-fluorophenyl) -1-[4- (methylsulfonyl)phenyl] -1H-pyrrole;

4-[2-(4-fluorophenyl)-1H-pyrrol-1-yl]benzenesulfonamide;

1-(4-fluorophenyl)-2-[4-(methylsulfonyl)phenyl]-1H-pyrrole;

4-[1-(4-fluorophenyl)-5-methyl-1H-pyrrol-2-yl]benzenesulfonamide;

ethyl 1-(4-fluorophenyl) -5-[4-(methylsulfonyl)phenyl]-1H-pyrrole-2-propanoate;

2,2,2-trifluoro-1-[1-(4-fluorophenyl) -2-methyl-S-[4-(methylsulfonyl)phenyl--1H-pyrrol-3-yl]ethanone;

1-[1-(4-fluorophenyl)-2-methyl-5-[4-(methylsulfonyl)phenyl]-1H-pyrrol-3-yl]ethanone;

1-(4-fluorophenyl)-2-methyl-5-[4-(methylsulfonyl)phenyl]l-3-[(trifluoromethyl) sulfonyl] -1H-pyrrole;

1-(4-fluorophenyl)-2-methyl-5-[4-(methylsulfonyl)phenyl]-1H-pyrrole-3-carbonitrile;

1-(4-fluorophenyl)-2-methyl-5-[4-(methylsulfonyl)phenyl]-1H-pyrrole-3-carboxaldehyde;

3-bromo-1-(4-fluorophenyl)-2-methyl-5-[4-(methylsulfonyl)phenyl]-1H-pyrrole;

3-chloro-1-(4-fluorophenyl)-2-methyl-5-[-4-(methylsulfonyl)phenyl]-1H-pyrrole;

1-(4-fluorophenyl)-2-methyl-5-[4-(methylsulfonyl)phenyl]-1H-pyrrole-3-methanol;

[1-(4-fluorophenyl)-2-methyl-5-[4-(methylsulfonyl)phenyl]-1H-pyrrol-3-yl]methyl acetate;

1-(4-fluorophenyl)-2-methyl-5-[4-(methylsulfonyl)phenyl] -α,α,α- (trifluoromethyl)-1H-pyrrole-3-methanol; and 1-(4-fluorophenyl)-2-methyl-5-[4-(methylsulfonyl)phenyl] -3-(2,2,2-trifluoroethyl)-1H-pyrrole.

5. A compound selected from compounds, and their pharmaceutically acceptable salts, of the group consisting of 3-[(3-chlorophenoxy)methyl]-1-(4-fluorophenyl)-2-methyl-5-[4-methylsulfonyl)phenyl]-1H-pyrrole; 1-(4-fluorophenyl)-2-methyl-5-[4-(methylsulfonyl)phenyl]-1H-pyrrol-3-yl]-phenylmethanone; and 3-[(4-chlorophenoxy)methyl]-1-(4-fluorophenyl)-2-methyl-S-[4-(methylsulfonyl)phenyl]-1H-pyrrole.

6. A compound of Formula II

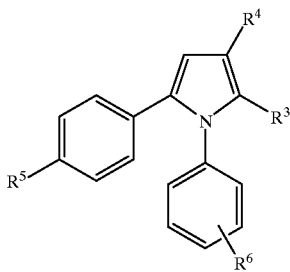

II wherein $R^3$ is a radical selected from hydrido, methyl and lower alkoxycarbonylalkyl; wherein $R^4$ is a radical selected from hydrido, halo, cyano, formyl, lower haloalkylsulfonyl, lower haloalkyl, lower hydroxyalkyl, lower alkylcarbonyl, lower haloalkylcarbonyl, lower alkylcarbonyloxyalkyl and lower haloalkylhydroxyalkyl; wherein $R^5$ is methylsulfonyl or aminosulfonyl; and wherein $R^6$ is one or more radicals independently selected from hydrido, halo, lower alkyl, lower alkylcarbonyl, and lower haloalkyl; or a pharmaceutically-acceptable salt thereof.

7. Compound of claim 6 wherein $R^3$ is a radical selected from hydrido, methyl and ethoxycarbonylethyl; wherein $R^4$ is a radical selected from hydrido, trifluoroethyl, chloro, bromo, formyl, cyano, trifluoromethylsulfonyl, hydroxymethyl, methylcarbonyl, trifluoromethylcarbonyl, trifluoro(hydroxy)ethyl and methylcarbonyloxymethyl; wherein $R^5$ is methylsulfonyl or aminosulfonyl; and wherein $R^6$ is one or more radicals independently selected from hydrido, fluoro, chloro, methyl, ethyl, trifluoromethyl and methylcarbonyl; or a pharmaceutically-acceptable salt thereof.

8. A compound of Formula III

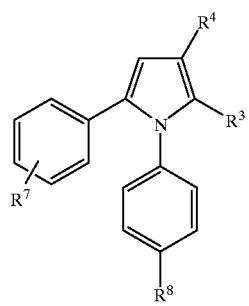

III wherein $R^3$ is hydrido; wherein $R^4$ is a radical selected from hydrido, halo, cyano, formyl, lower haloalkylsulfonyl, lower haloalkyl, lower hydroxyalkyl, lower alkylcarbonyl, lower haloalkylcarbonyl, lower alkylcarbonyloxyalkyl and lower haloalkylhydroxyalkyl; wherein $R^7$ is one or more radicals independently selected from hydrido, halo, lower alkyl, lower alkylcarbonyl, and lower haloalkyl; and wherein $R^8$ is methylsulfonyl or aminosulfonyl; or a pharmaceutically-acceptable salt thereof.

9. Compound of claim 8 wherein $R^3$ is hydrido; wherein $R^4$ is a radical selected from hydrido, trifluoroethyl, chloro, bromo, formyl, cyano, trifluoromethylsulfonyl, hydroxymethyl, methylcarbonyl, trifluoromethylcarbonyl, trifluoro(hydroxy)ethyl and methylcarbonyloxymethyl; wherein $R^7$ is one or more radicals independently selected from hydrido, fluoro, chloro, methyl, ethyl, trifluoromethyl and methylcarbonyl; and wherein $R^8$ is methylsulfonyl or aminosulfonyl; or a pharmaceutically-acceptable salt thereof.

10. A pharmaceutical composition comprising a therapeutically-effective amount of a compound, said compound selected from a family of compounds of claim 1; or a pharmaceutically-acceptable salt thereof.

11. A pharmaceutical composition comprising a therapeutically-effective amount of a compound, said compound selected from a family of compounds of claim 2; or a pharmaceutically-acceptable salt thereof.

12. A pharmaceutical composition comprising a therapeutically-effective amount of a compound, said compound selected from a family of compounds of claim 3; or a pharmaceutically-acceptable salt thereof.

13. A pharmaceutical composition comprising a therapeutically-effective amount of a compound, said compound selected from a family of compounds of claim 4; or a pharmaceutically-acceptable salt thereof.

14. A pharmaceutical composition comprising a therapeutically-effective amount of a compound, said compound selected from a family of compounds of claim 5; or a pharmaceutically-acceptable salt thereof.

15. A pharmaceutical composition comprising a therapeutically-effective amount of a compound, said compound selected from a family of compounds of claim 6; or a pharmaceutically-acceptable salt thereof.

16. A pharmaceutical composition comprising a therapeutically-effective amount of a compound, said compound selected from a family of compounds of claim 7; or a pharmaceutically-acceptable salt thereof.

17. A pharmaceutical composition comprising a therapeutically-effective amount of a compound, said compound selected from a family of compounds of claim 8; or a pharmaceutically-acceptable salt thereof.

18. A pharmaceutical composition comprising a therapeutically-effective amount of a compound, said compound selected from a family of compounds of claim 9; or a pharmaceutically-acceptable salt thereof.

19. A method of treating a cyclooxygenase-2 mediated disorder in a subject, said method comprising treating the subject having or susceptible to said disorder with a therapeutically-effective amount of a compound of claim 1; or a pharmaceutically-acceptable salt thereof.

20. A method of treating a cyclooxygenase-2 mediated disorder in a subject, said method comprising treating the subject having or susceptible to said disorder with a therapeutically-effective amount of a compound of claim 2; or a pharmaceutically-acceptable salt thereof.

21. A method of treating a cyclooxygenase-2 mediated disorder in a subject, said method comprising treating the subject having or susceptible to said disorder with a therapeutically-effective amount of a compound of claim 3; or a pharmaceutically-acceptable salt thereof.

22. A method of treating a cyclooxygenase-2 mediated disorder in a subject, said method comprising treating the subject having or susceptible to said disorder with a therapeutically-effective amount of a compound of claim 4; or a pharmaceutically-acceptable salt thereof.

23. A method of treating a cyclooxygenase-2 mediated disorder in a subject, said method comprising treating the subject having or susceptible to said disorder with a therapeutically-effective amount of a compound of claim 5; or a pharmaceutically-acceptable salt thereof.

24. A method of treating a cyclooxygenase-2 mediated disorder in a subject, said method comprising treating the subject having or susceptible to said disorder with a therapeutically-effective amount of a compound of claim 6; or a pharmaceutically-acceptable salt thereof.

25. A method of treating a cyclooxygenase-2 mediated disorder in a subject, said method comprising treating the subject having or susceptible to said disorder with a therapeutically-effective amount of a compound of claim 7; or a pharmaceutically-acceptable salt thereof.

26. A method of treating a cyclooxygenase-2 mediated disorder in a subject, said method comprising treating the subject having or susceptible to said disorder with a therapeutically-effective amount of a compound of claim 8; or a pharmaceutically-acceptable salt thereof.

27. A method of treating a cyclooxygenase-2 mediated disorder in a subject, said method comprising treating the subject having or susceptible to said disorder with a therapeutically-effective amount of a compound of claim 9; or a pharmaceutically-acceptable salt thereof.

28. The method of claim 19 wherein the cyclooxygenase-2 mediated disorder is inflammation.

29. The method of claim 19 wherein the cyclooxygenase-2 mediated disorder is arthritis.

30. The method of claim 19 wherein the cyclooxygenase-2 mediated disorder is pain.

31. The method of claim 19 wherein the cyclooxygenase-2 mediated disorder is fever.

* * * * *